United States Patent
Matsumoto et al.

(10) Patent No.: US 12,277,728 B2
(45) Date of Patent: Apr. 15, 2025

(54) PUPIL DETECTION DEVICE, LINE-OF-SIGHT DETECTION DEVICE, OCCUPANT MONITORING SYSTEM, AND PUPIL DETECTION METHOD

(71) Applicant: Mitsubishi Electric Corporation, Tokyo (JP)

(72) Inventors: Atsushi Matsumoto, Tokyo (JP); Ryosuke Torama, Tokyo (JP); Shintaro Watanabe, Tokyo (JP); Ryohei Murachi, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 361 days.

(21) Appl. No.: 17/790,678

(22) PCT Filed: Jan. 8, 2020

(86) PCT No.: PCT/JP2020/000213
§ 371 (c)(1),
(2) Date: Jul. 1, 2022

(87) PCT Pub. No.: WO2021/140579
PCT Pub. Date: Jul. 15, 2021

(65) Prior Publication Data
US 2023/0043992 A1    Feb. 9, 2023

(51) Int. Cl.
*G06T 7/73* (2017.01)
*A61B 3/113* (2006.01)
(Continued)

(52) U.S. Cl.
CPC ............... *G06T 7/74* (2017.01); *G06V 10/60* (2022.01); *G06V 20/597* (2022.01); *G06V 40/19* (2022.01);
(Continued)

(58) Field of Classification Search
CPC ............. G06T 7/74; G06T 2207/30201; G06T 2207/30244; G06T 2207/30268;
(Continued)

(56) References Cited

U.S. PATENT DOCUMENTS

2003/0118217 A1    6/2003   Kondo et al.
2011/0249868 A1    10/2011  Tsukizawa et al.
(Continued)

FOREIGN PATENT DOCUMENTS

JP    2002-056394 A    2/2002
JP    2012-024154 A    2/2012
WO    2010/035472 A1   4/2010

OTHER PUBLICATIONS

International Search Report of PCT/JP2020/000213 dated Mar. 31, 2020 [PCT/ISA/210].
(Continued)

*Primary Examiner* — Siamak Harandi
*Assistant Examiner* — Andrew S Budisalich
(74) *Attorney, Agent, or Firm* — Saghrue Mion, PLLC

(57) ABSTRACT

A pupil detection device includes an eye area image obtaining unit that obtains image data representing an eye area image in a captured image obtained by a camera; a luminance gradient calculating unit that calculates luminance
(Continued)

gradient vectors corresponding to respective individual image units in the eye area image, using the image data; an evaluation value calculating unit that calculates evaluation values corresponding to the respective individual image units, using the luminance gradient vectors; and a pupil location detecting unit that detects a pupil location in the eye area image, using the evaluation values.

20 Claims, 19 Drawing Sheets

(51) Int. Cl.
*A61B 5/18* (2006.01)
*G06V 10/60* (2022.01)
*G06V 20/59* (2022.01)
*G06V 40/18* (2022.01)
*G06V 40/19* (2022.01)

(52) U.S. Cl.
CPC .. *G06V 40/193* (2022.01); *G06T 2207/30201* (2013.01); *G06T 2207/30244* (2013.01); *G06T 2207/30268* (2013.01)

(58) Field of Classification Search
CPC ...... G06V 10/60; G06V 20/597; G06V 40/19; G06V 40/193; A61B 3/113; A61B 5/18
See application file for complete search history.

(56) References Cited

U.S. PATENT DOCUMENTS

| | | | | |
|---|---|---|---|---|
| 2012/0045100 | A1* | 2/2012 | Ishigami | G06T 7/73 382/106 |
| 2012/0177266 | A1* | 7/2012 | Tsukizawa | G06T 7/73 382/128 |
| 2014/0043459 | A1 | 2/2014 | Tsukizawa et al. | |
| 2014/0072230 | A1* | 3/2014 | Ruan | G06T 7/12 382/199 |
| 2016/0272215 | A1* | 9/2016 | Laine | G06V 20/597 |
| 2017/0286771 | A1* | 10/2017 | Ishii | A61B 3/113 |
| 2018/0144179 | A1* | 5/2018 | Hatakeyama | G06V 10/752 |
| 2019/0065710 | A1* | 2/2019 | Hama | G06F 21/31 |

OTHER PUBLICATIONS

Communication dated Nov. 15, 2022, issued inn Japanese Application No. 2021-569641.

* cited by examiner

PUPIL DETECTION DEVICE, LINE-OF-SIGHT DETECTION DEVICE, OCCUPANT MONITORING SYSTEM, AND PUPIL DETECTION METHOD

CROSS REFERENCE TO RELATED APPLICATIONS

This application is a National Stage of International Application No. PCT/JP2020/000213 filed on Jan. 8, 2020.

TECHNICAL FIELD

The present disclosure relates to a pupil detection device, a line-of-sight detection device, an occupant monitoring system, and a pupil detection method.

BACKGROUND ART

Conventionally, there is developed a technique for detecting a pupil location in an image captured by a camera (which may be hereinafter referred to as "captured image".). In addition, there is developed a technique for detecting a line-of-sight direction on the basis of the detected pupil location (see, for example, Patent Literature 1.). These techniques are used in, for example, a driver monitoring system (DMS) or an occupant monitoring system (OMS).

Here, the DMS is a system for monitoring a state of a driver. On the other hand, the OMS is a system for monitoring a state of at least one of a driver and a passenger. At least one of the driver and passenger may be hereinafter collectively referred to as "occupant". Namely, the occupant is a broader term for the driver.

CITATION LIST

Patent Literatures

Patent Literature 1: JP 2012-24154 A

SUMMARY OF INVENTION

Technical Problem

A pupil detection device described in Patent Literature 1 detects a corneal reflection image in a captured image, and detects a pupil location using the detected corneal reflection image (see, for example, the abstract of Patent Literature 1.). Hence, there is a problem that when a corneal reflection image is not detected normally, a pupil location cannot be detected.

For example, a corneal reflection image may not be detected normally due to a low resolution of a camera. In addition, for example, a corneal reflection image may not be detected normally due to a large distance between a camera position and an occupant head's position. In addition, for example, a state in which a corneal reflection image is not included in a captured image may occur depending on a positional relationship between the camera and the occupant's head. As a result, a corneal reflection image may not be detected. In such a case, the pupil detection device described in Patent Literature 1 has a problem of not being able to detect a pupil location.

The present disclosure is made to solve a problem such as that described above, and an object of the present disclosure is to eliminate the need to detect a corneal reflection image upon detecting a pupil location.

Solution to Problem

A pupil detection device according to the present disclosure includes processing circuitry to obtain image data representing an eye area image in an image captured by a camera; to calculate luminance gradient vectors corresponding to respective individual image units in the eye area image, using the image data; to calculate evaluation values corresponding to the respective individual image units, using the luminance gradient vectors; and to detect a pupil location in the eye area image, using the evaluation values.

Advantageous Effects of Invention

According to the present disclosure, it is configured in the above-described manner, and thus, upon detecting a pupil location, the need to detect a corneal reflection image can be eliminated.

DESCRIPTION OF EMBODIMENTS

To describe the disclosure in more detail, embodiments for carrying out the disclosure will be described below with reference to the accompanying drawings.

First Embodiment

Figure 1:
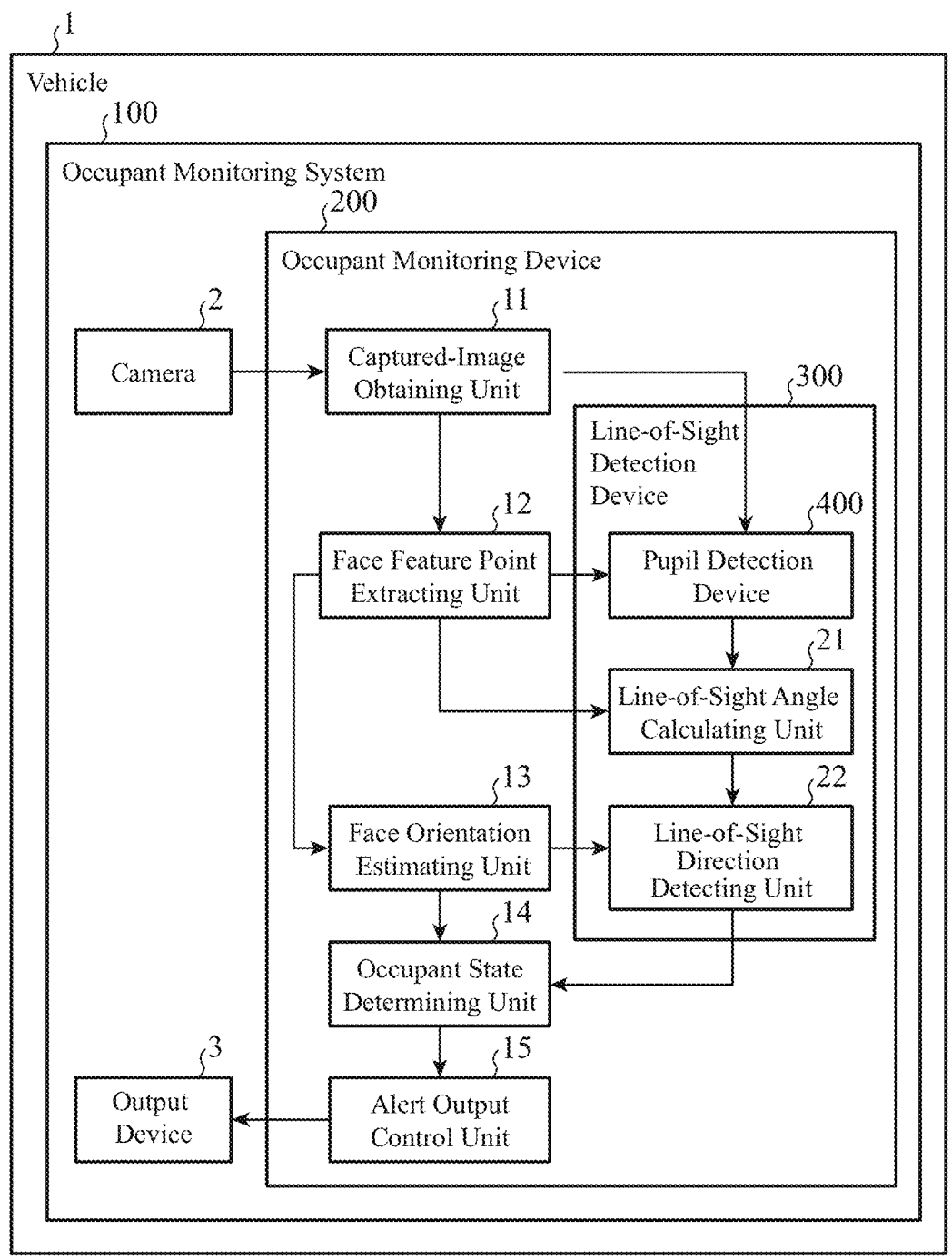
FIG. 1 is a block diagram showing a main part of an occupant monitoring system according to a first embodiment.
Figure 2:
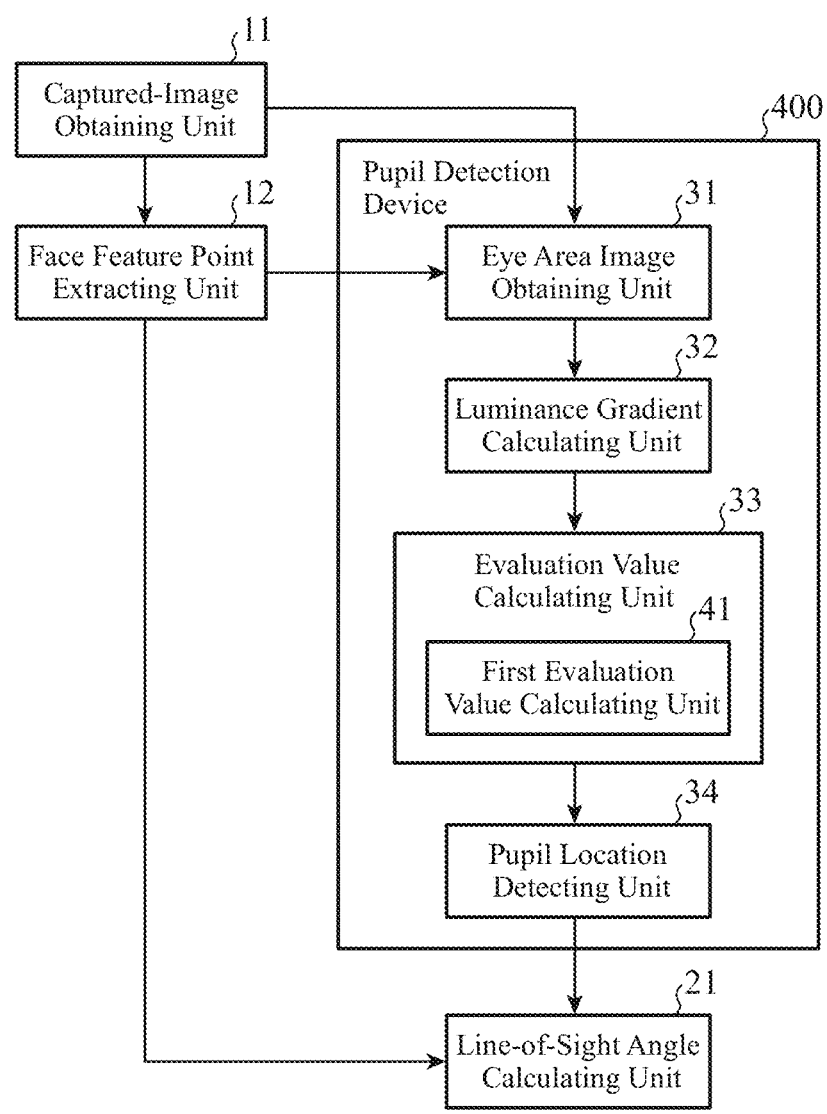
FIG. 2 is a block diagram showing a main part of a pupil detection device in the occupant monitoring system according to the first embodiment.

FIG. 1 is a block diagram showing a main part of an occupant monitoring system according to a first embodiment. FIG. 2 is a block diagram showing a main part of a pupil detection device in the occupant monitoring system according to the first embodiment. With reference to FIGS. 1 and 2, the occupant monitoring system according to the first embodiment will be described.

As shown in FIG. 1, a camera 2 and an output device 3 are provided in a vehicle 1.

The camera 2 includes a camera for capturing a vehicle's interior. Namely, the camera 2 is provided at a front portion in the interior of the vehicle 1. Specifically, for example, the camera 2 is provided at a location on a dashboard of the vehicle 1 near a center console or at a location on the dashboard of the vehicle 1 near a steering column. An area captured by the camera 2 (hereinafter, referred to as "captured area".) includes a driver's seat of the vehicle 1. Thus, when a driver is seated in the driver's seat of the vehicle 1, an image including a driver's face is captured. In addition to the driver's seat, the captured area may include a passenger seat of the vehicle 1. As a result, when a passenger is seated in the passenger seat of the vehicle 1, an image including a passenger's face is captured.

Of occupants of the vehicle 1, an occupant to be captured by the camera 2 may be hereinafter referred to as "capturing target person". Namely, the capturing target person indicates the driver of the vehicle 1. Alternatively, the capturing target person indicates each of the driver of the vehicle 1 and a passenger of the vehicle 1.

The output device 3 includes at least one of a display, a speaker, and a wireless communication device. The display includes, for example, a liquid crystal display, an organic electroluminescence (EL) display, or a head-up display. The display is provided on, for example, the dashboard of the vehicle 1. The speaker is provided on, for example, the dashboard of the vehicle 1. The wireless communication device includes a transmitter and a receiver.

As shown in FIG. 1, an occupant monitoring system 100 includes the camera 2, the output device 3, and an occupant monitoring device 200. The occupant monitoring device 200 includes a captured-image obtaining unit 11, a face feature point extracting unit 12, a face orientation estimating unit 13, an occupant state determining unit 14, an alert output control unit 15, and a line-of-sight detection device 300. The line-of-sight detection device 300 includes a line-of-sight angle calculating unit 21, a line-of-sight direction detecting unit 22, and a pupil detection device 400. As shown in FIG. 2, the pupil detection device 400 includes an eye area image obtaining unit 31, a luminance gradient calculating unit 32, an evaluation value calculating unit 33, and a pupil location detecting unit 34. The evaluation value calculating unit 33 includes a first evaluation value calculating unit 41.

The captured-image obtaining unit 11 obtains image data representing a captured image I1 obtained by the camera 2 (hereinafter, referred to as "first image data".). The captured-image obtaining unit 11 outputs the obtained first image data to the face feature point extracting unit 12 and the eye area image obtaining unit 31.

The face feature point extracting unit 12 obtains the first image data outputted from the captured-image obtaining unit 11. The face feature point extracting unit 12 extracts a plurality of face feature points in the captured image I1, using the obtained first image data. The face feature point extracting unit 12 outputs information indicating the extracted plurality of face feature points (hereinafter, referred to as "face feature point information".) to the face orientation estimating unit 13. For the extraction of individual face feature points, various publicly known techniques can be used. A detailed description of the techniques is omitted.

Any one of a left eye of a capturing target person and a right eye of the capturing target person is hereinafter referred to as "line-of-sight detection target eye". Alternatively, each of the left eye of the capturing target person and the right eye of the capturing target person is referred to as "line-of-sight detection target eye".

The plurality of face feature points extracted by the face feature point extracting unit 12 include a feature point FP1 corresponding to an outer corner of the line-of-sight detection target eye (hereinafter, referred to as "first feature point".); a feature point FP2 corresponding to an inner corner of the line-of-sight detection target eye (hereinafter, referred to as "second feature point".); a feature point FP3 corresponding to an upper eyelid of the line-of-sight detection target eye (hereinafter, referred to as "third feature point".); and a feature point FP4 corresponding to a lower eyelid of the line-of-sight detection target eye (hereinafter, referred to as "fourth feature point".). The face feature point extracting unit 12 outputs information indicating the extracted first feature point FP1, second feature point FP2, third feature point FP3, and fourth feature point FP4 (hereinafter, referred to as "eye feature point information".) to the line-of-sight angle calculating unit 21 and the eye area image obtaining unit 31.

The face orientation estimating unit 13 obtains the face feature point information outputted from the face feature point extracting unit 12. The face orientation estimating unit 13 estimates a face orientation of the capturing target person, using the obtained face feature point information. The face orientation estimating unit 13 outputs information indicating the estimated face orientation (hereinafter, referred to as "face orientation information".) to the occupant state determining unit 14 and the line-of-sight direction detecting unit 22.

More specifically, the face orientation estimating unit 13 calculates a vector V1 representing the face orientation of the capturing target person (hereinafter, referred to as "face orientation vector".), using the obtained face feature point information. The face orientation information includes the calculated face orientation vector V1. For the calculation of the face orientation vector V1, various publicly known techniques can be used. A detailed description of the techniques is omitted.

The eye area image obtaining unit 31 obtains the eye feature point information outputted from the face feature point extracting unit 12. The eye area image obtaining unit 31 detects an area including the line-of-sight detection target eye (hereinafter, referred to as "eye area".) in the captured image I1, using the obtained eye feature point information. For the detection of an eye area, various publicly known techniques can be used. A detailed description of the techniques is omitted.

In addition, the eye area image obtaining unit 31 obtains the first image data outputted from the captured-image obtaining unit 11. The eye area image obtaining unit 31 obtains image data (hereinafter, referred to as "second image data.") representing an image (hereinafter, referred to as "eye area image".) I2 corresponding to the eye area in the captured image I1, using the obtained first image data. The eye area image obtaining unit 31 outputs the obtained second image data to the luminance gradient calculating unit 32.

Figure 3:
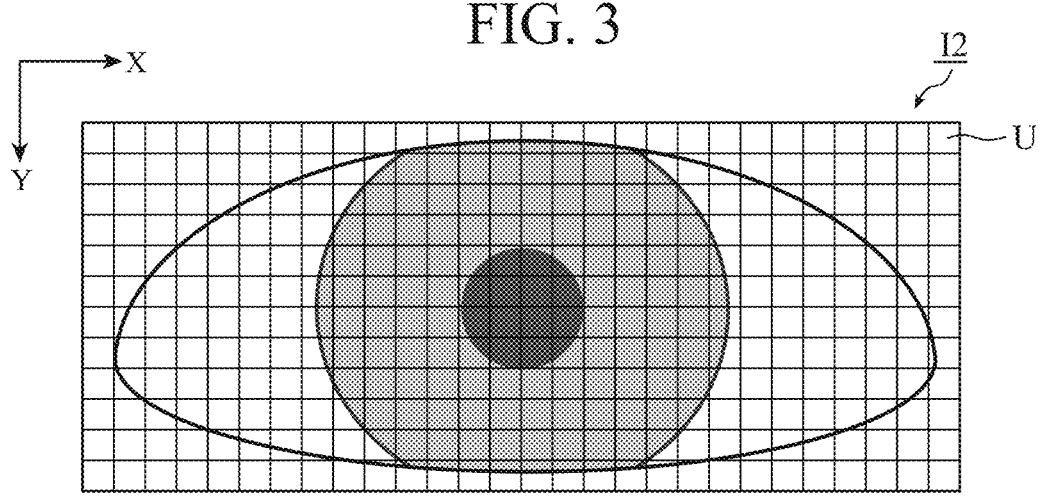
FIG. 3 is an explanatory diagram showing an example of an eye area image.

FIG. 3 shows an example of an eye area image I2. As shown in FIG. 3, the eye area image I2 includes a plurality of units (hereinafter, referred to as "image units".) U arranged in two directions orthogonal to each other (i.e., an X-direction and a Y-direction). Here, each individual image unit U includes one pixel. Alternatively, each individual image unit U includes a plurality of pixels adjacent to each other.

The luminance gradient calculating unit 32 obtains the second image data outputted from the eye area image obtaining unit 31. The luminance gradient calculating unit 32 calculates luminance gradient vectors V2 corresponding to respective individual image units U in the eye area image I2, using the obtained second image data. The luminance gradient calculating unit 32 outputs information indicating the calculated luminance gradient vectors V2 (hereinafter, referred to as "luminance gradient information".) to the evaluation value calculating unit 33.

Figure 4:
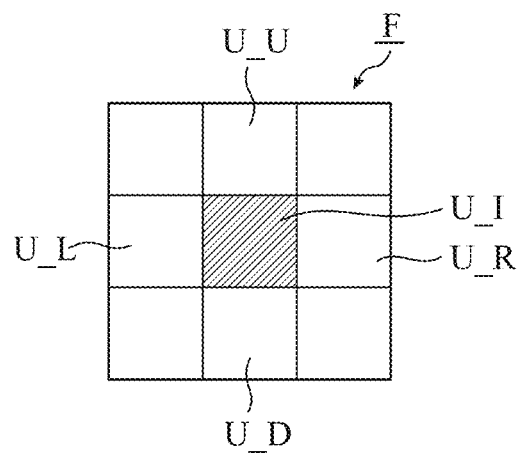
FIG. 4 is an explanatory diagram showing an example of a filter.
Figure 5:
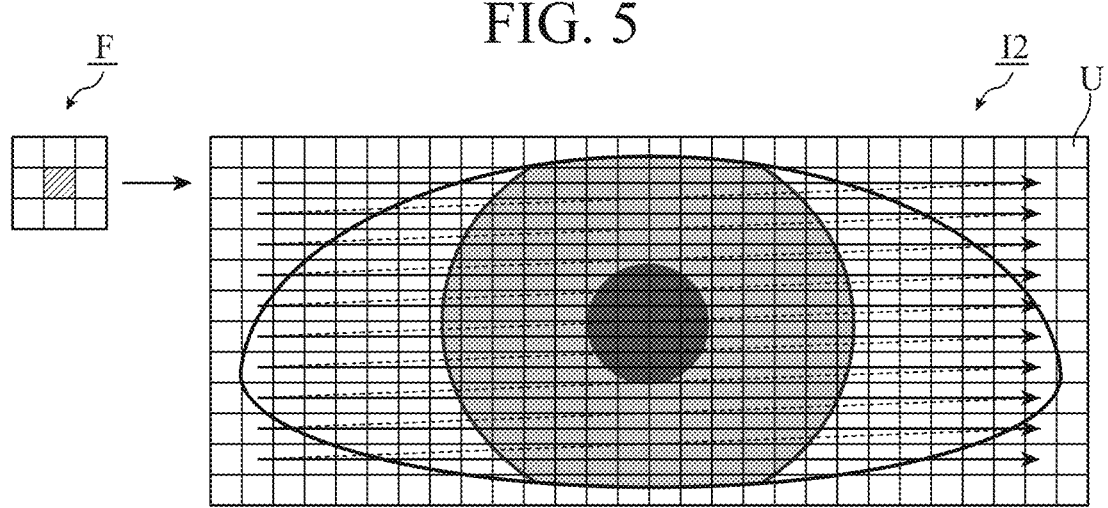
FIG. 5 is an explanatory diagram showing an example of scanning by the filter.

Now, with reference to FIGS. 4 to 8, a method of calculating a luminance gradient vector V2 will be described. For the calculation of a luminance gradient vector V2, a filter F shown in FIG. 4 is used. As shown in FIG. 5, the filter F is applied in such a manner that the filter F scans the eye area image I2.

The filter F calculates, for each individual image unit (which may be hereinafter referred to as "focused image unit".) U_I in the eye area image I2, a difference value (hereinafter, referred to as "first luminance gradient value".) $\Delta B\_X$ between a luminance value B_L of an image unit U_L disposed to the left of the focused image unit U_I and a luminance value B_R of an image unit U_R disposed to the right of the focused image unit U_I. In addition, the filter F calculates a difference value (hereinafter, referred to as "second luminance gradient value".) $\Delta B\_Y$ between a luminance value B_U of an image unit U_U disposed above the focused image unit U_I and a luminance value B_D of an image unit U_D disposed below the focused image unit U_I.

Figure 6:
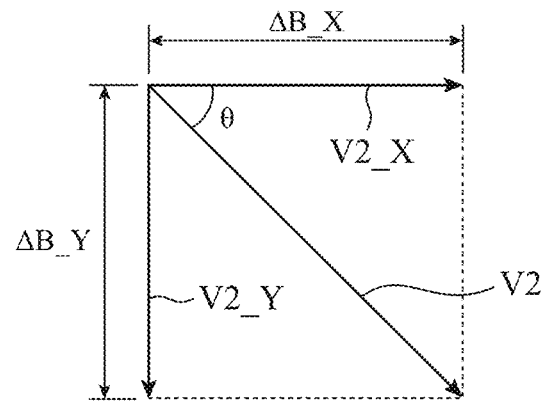
FIG. 6 is an explanatory diagram showing an example of a vector corresponding to a first luminance gradient value, an example of a vector corresponding to a second luminance gradient value, and an example of a luminance gradient vector.

As shown in FIG. 6, a luminance gradient vector V2 is represented by the sum of a vector V2_X corresponding to a first luminance gradient value $\Delta B\_X$ and a vector V2_Y corresponding to a second luminance gradient value $\Delta B\_Y$. Hence, the filter F calculates an angle (hereinafter, referred to as "luminance gradient angle".) $\theta$ corresponding to the direction of the luminance gradient vector V2, using the above-described calculated first luminance gradient value $\Delta B\_X$ and the above-described calculated second luminance gradient value $\Delta B\_Y$. The luminance gradient information includes the calculated luminance gradient angles $\theta$.

Figure 7:
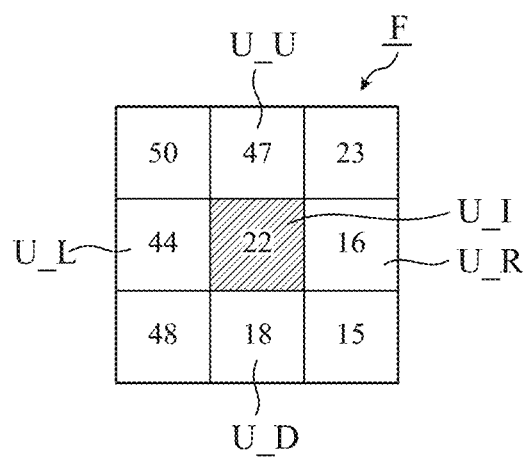
FIG. 7 is an explanatory diagram showing an example of a luminance value of a focused image unit and an example of luminance values of individual image units arranged around the focused image unit.
Figure 8:
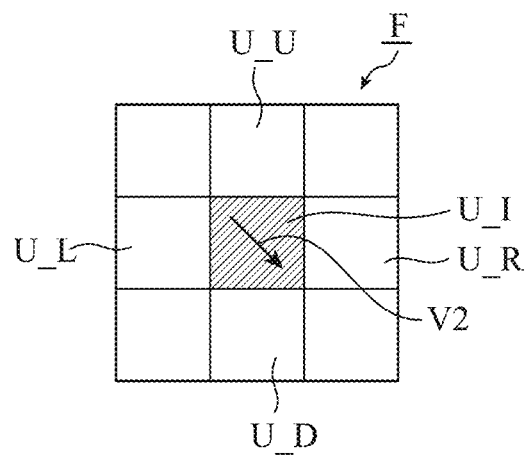
FIG. 8 is an explanatory diagram showing an example of a luminance gradient vector corresponding to the focused image unit.

For example, as shown in FIG. 7, it is assumed that the luminance value B_L is 44, the luminance value B_R is 16, the luminance value B_U is 47, and the luminance value B_D is 18. In this case, by applying the filter F to the focused image unit U_I, the first luminance gradient value $\Delta B\_X$ is calculated as −28 and the second luminance gradient value $\Delta B\_Y$ is calculated as −29. In addition, the luminance gradient angle $\theta$ is calculated as 46°. FIG. 8 shows an example of a luminance gradient vector V2 based on these values.

The evaluation value calculating unit 33 obtains the luminance gradient information outputted from the luminance gradient calculating unit 32. The evaluation value calculating unit 33 calculates evaluation values E corresponding to respective individual image units U in the eye area image I2, using the obtained luminance gradient information. The evaluation value calculating unit 33 outputs information including the calculated evaluation values E (hereinafter, referred to as "evaluation value information".) to the pupil location detecting unit 34.

Figure 9:
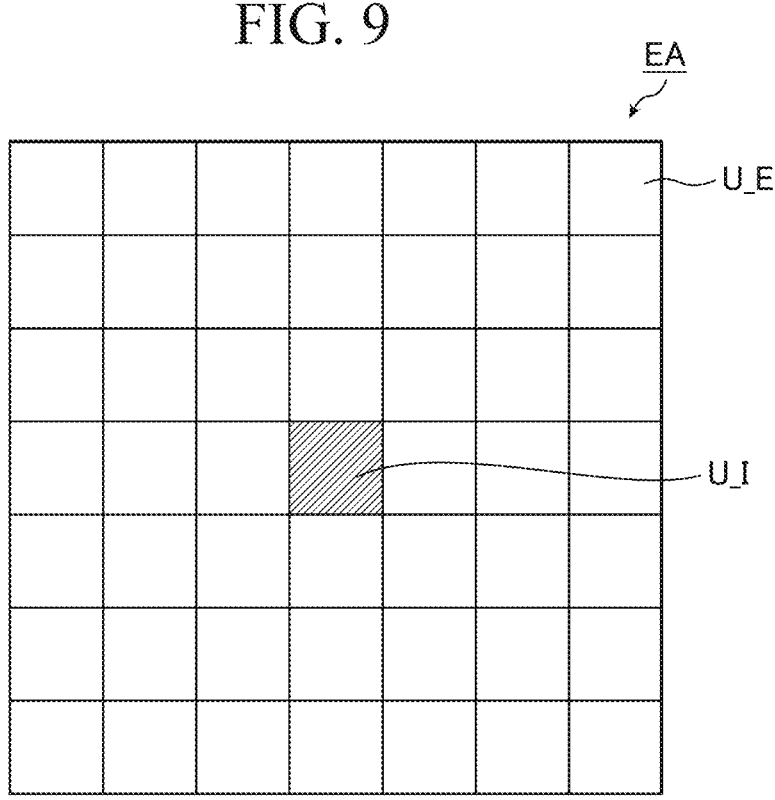
FIG. 9 is an explanatory diagram showing an example of an evaluation area.
Figure 10:
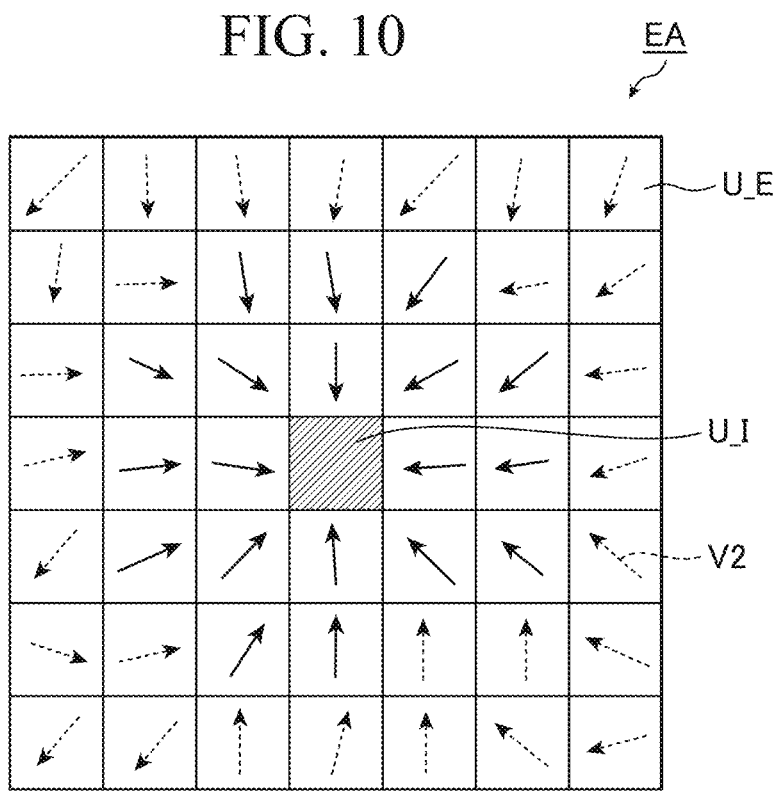
FIG. 10 is an explanatory diagram showing an example of luminance gradient vectors corresponding to individual evaluation image units.

Here, the evaluation values E calculated by the evaluation value calculating unit 33 each include a first evaluation value E1 calculated by the first evaluation value calculating unit 41. Namely, the evaluation value information includes the calculated first evaluation values E1. The first evaluation values E1 are each based on the number n of luminance gradient vectors V2 directed toward a corresponding one of the individual image units U (i.e., a focused image unit U_I). With reference to FIGS. 9 and 10, a method of calculating a first evaluation value E1 will be described.

First, the first evaluation value calculating unit 41 sets an area for evaluation (hereinafter, referred to as "evaluation area".) EA that includes a focused image unit U_I. The evaluation area EA includes the focused image unit U_I and includes N image units (which may be hereinafter referred to as "evaluation image units".) U_E different from the focused image unit U_I. N is any integer greater than or equal to 2.

FIG. 9 shows an example of an evaluation area EA. In the example shown in FIG. 9, the evaluation area EA has a square shape and has a focused image unit U_I disposed at a central portion of the evaluation area EA. In addition, the evaluation area EA includes 48 evaluation image units U_E. Namely, N=48.

The evaluation area EA has a size smaller than a predetermined size (hereinafter, referred to as "reference iris size".). The reference iris size corresponds to the standard size of the human iris.

Then, the first evaluation value calculating unit 41 calculates angles θ' corresponding to the slopes of straight lines each of which connects the focused image unit U_I to a corresponding individual evaluation image unit U_E. Then, the first evaluation value calculating unit 41 calculates, for each individual evaluation image unit U_E, a difference value Δθ between a corresponding luminance gradient angle θ and a corresponding angle θ'. When the calculated difference value Δθ is less than a predetermined threshold value Δθth, the first evaluation value calculating unit 41 determines that a corresponding luminance gradient vector V2 has a direction oriented toward the focused image unit U_I. On the other hand, when the calculated difference value Δθ is greater than or equal to the threshold value Δθth, the first evaluation value calculating unit 41 determines that the corresponding luminance gradient vector V2 does not have a direction oriented toward the focused image unit U_I.

Then, the first evaluation value calculating unit 41 calculates the number n of luminance gradient vectors V2 directed toward the focused image unit U_I, on the basis of results of the determination. In this case, the number n is calculated as a value between 0 and N, inclusive. The evaluation value calculating unit 33 calculates a first evaluation value E1 based on the calculated number n. Namely, the first evaluation value E1 is calculated as a larger value for a larger number n. In other words, the first evaluation value E1 is calculated as a smaller value for a smaller number n.

For example, as shown in FIG. 10, it is assumed that an evaluation area EA includes 48 evaluation image units U_E (N=48). It is assumed that of 48 luminance gradient vectors V2 corresponding to the 48 evaluation image units U_E, 19 luminance gradient vectors V2 have a direction oriented toward a focused image unit U_I (n=19). In the drawing, a solid arrow indicates a luminance gradient vector V2 having a direction oriented toward the focused image unit U_I. On the other hand, a dashed arrow indicates a luminance gradient vector V2 that does not have a direction oriented toward the focused image unit U_I.

In this case, the first evaluation value calculating unit 41 calculates the number n as 19. In addition, the first evaluation value calculating unit 41 calculates a first evaluation value E1 based on the calculated number n. For example, a first evaluation value E1 based on n/N is calculated.

The pupil location detecting unit 34 obtains the evaluation value information outputted from the evaluation value calculating unit 33. The pupil location detecting unit 34 detects a pupil location PP in the eye area image I2, using the obtained evaluation value information. The pupil location detecting unit 34 outputs information indicating the detected pupil location PP (hereinafter, referred to as "pupil location information".) to the line-of-sight angle calculating unit 21.

More specifically, the pupil location detecting unit 34 detects coordinate values C_X and C_Y indicating the location of an image unit U corresponding to a pupil location PP in the eye area image I2, using the obtained evaluation value information. The pupil location information includes the detected coordinate values C_X and C_Y.

Specifically, the pupil location detecting unit 34 detects the largest value among a plurality of first evaluation values E1 corresponding to a plurality of image units U in the eye area image I2. In other words, the pupil location detecting unit 34 detects the maximum value of the plurality of first evaluation values E1. The pupil location detecting unit 34 detects coordinate values C_X and C_Y indicating the location of an image unit U corresponding to the detected maximum value. As a result, the coordinate values CX and C_Y corresponding to a pupil location PP are detected.

Now, principles of detecting a pupil location PP by detection of the largest value (i.e., the maximum value) will be described.

Firstly, normally, the eye area image I2 includes an area corresponding to the inside of a palpebral fissure (hereinafter, referred to as "area inside the palpebral fissure".) and an area corresponding to the outside of the palpebral fissure (hereinafter, referred to as "area outside the palpebral fissure".). The area outside the palpebral fissure is disposed around the area inside the palpebral fissure. In addition, the area inside the palpebral fissure includes an area corresponding to a pupil (hereinafter, referred to as "pupil area".), an area corresponding to an iris (hereinafter, referred to as "iris area".), and an area corresponding to a sclera (hereinafter, referred to as "sclera area".). The sclera area is disposed around the iris area. The iris area is disposed around the pupil area. The iris area has a circular shape. The pupil area has a circular shape.

Secondly, normally, the luminance of the pupil area is low compared with the luminance of the iris area. Hence, in the area inside the palpebral fissure, an edge based on luminance discontinuity occurs at a boundary portion between the pupil area and the iris area. In addition, the luminance of the iris area is low compared with the luminance of the sclera area. Hence, in the area inside the palpebral fissure, an edge based on luminance discontinuity occurs at a boundary portion between the iris area and the sclera area.

Considering these principles, there is a high probability that the number n corresponding to an image unit U in the pupil area is large compared with the number n corresponding to an image unit U outside the pupil area. Thus, there is a high probability that first evaluation values E1 corresponding to the image units U in the pupil area are large compared with first evaluation values E1 corresponding to the image units U outside the pupil area. Thus, by detecting the largest value among the first evaluation values E1 (i.e., the maximum value of the first evaluation values E1), a pupil location PP can be detected.

The line-of-sight angle calculating unit 21 obtains the eye feature point information outputted from the face feature point extracting unit 12, and obtains the pupil location information outputted from the pupil location detecting unit 34. The line-of-sight angle calculating unit 21 calculates a line-of-sight angle ϕ of the capturing target person, using the obtained eye feature point information and the obtained pupil location information. The line-of-sight angle calculating unit 21 outputs information including the calculated line-of-sight angle ϕ (hereinafter, referred to as "line-of-sight angle information".) to the line-of-sight direction detecting unit 22.

Figure 11:
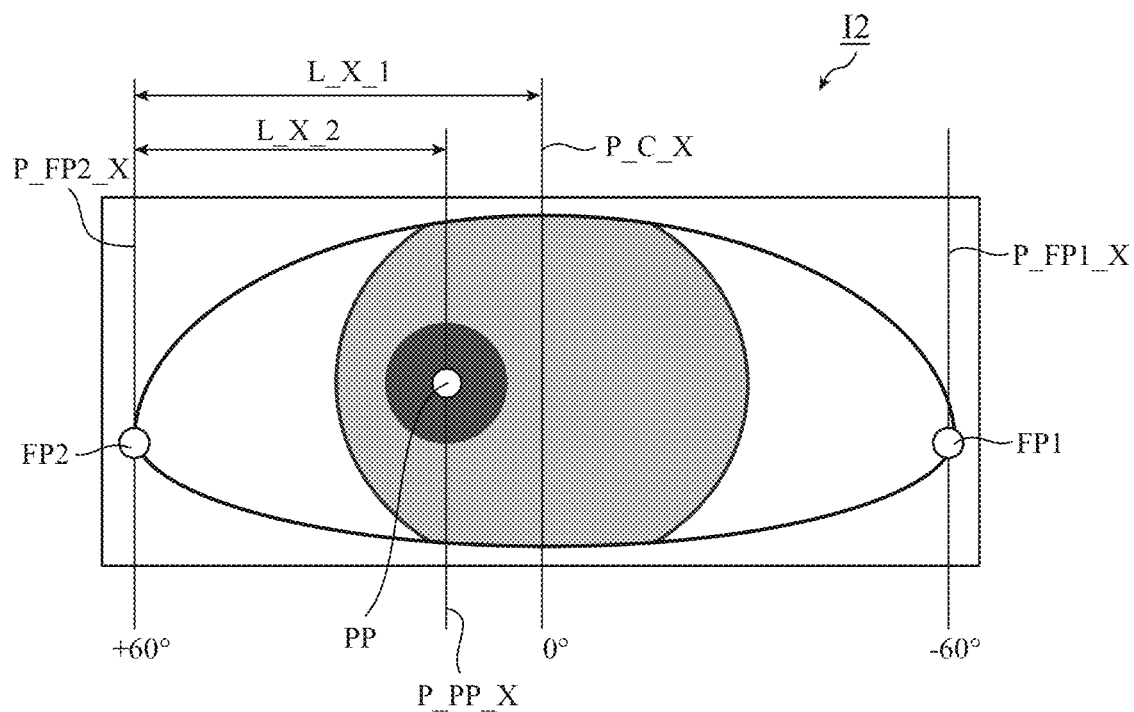
FIG. 11 is an explanatory diagram showing an example of a method of calculating a line-of-sight angle in a yaw direction.

Here, the line-of-sight angle ϕ includes a line-of-sight angle ϕ_X in a yaw direction and a line-of-sight angle ϕ_Y in a pitch direction. With reference to FIG. 11, a method of calculating the line-of-sight angle ϕ_X will be described. In addition, with reference to FIG. 12, a method of calculating the line-of-sight angle ϕ_Y will be described.

First, the line-of-sight angle calculating unit 21 calculates locations P_FP1_X and P_FP2_X in the X-direction, using the above-described obtained eye feature point information. The location P_FP1_X corresponds to the first feature point FP1 (i.e., the outer corner of the eye). The location P_FP2_X corresponds to the second feature point FP2 (i.e., the inner corner of the eye).

Then, the line-of-sight angle calculating unit 21 calculates a location (hereinafter, referred to as "first reference location".) P_C_X in the X-direction, on the basis of the calculated locations P_FP1_X and P_FP2_X. The first reference location P_C_X corresponds to an intermediate location between the first feature point FP1 and the second feature point FP2. Namely, the first reference location P_C_X corresponds to a central portion of the area inside the palpebral fissure in the X-direction.

Then, the line-of-sight angle calculating unit 21 calculates a location P_PP_X in the X-direction, using the above-described obtained pupil location information. The location P_PP_X corresponds to the pupil location PP.

Then, the line-of-sight angle calculating unit 21 calculates, for the location P_FP1_X or the location P_FP2_X, a distance L_X_1 to the first reference location P_C_X and a distance L_X_2 to the location P_PP_X. FIG. 11 shows an example of a case in which the location P_FP2_X is used as a reference for the distances L_X_1 and L_X_2.

In the line-of-sight angle calculating unit 21 there is preset a value indicating a maximum value ϕmax_X of the line-of-sight angle ϕ_X. Using the set maximum value ϕmax_X and the calculated distances L_X_1 and L_X_2, the line-of-sight angle calculating unit 21 calculates the line-of-sight angle ϕ_X by the following equation (1).

$$\phi\_X = \phi max\_X \times (L\_X\_1 - L\_X\_2)/L\_X\_1 \tag{1}$$

The maximum value ϕmax_X is based on, for example, the following model M_X. Specifically, in the model M_X, if the location P_PP_X is identical to the first reference location P_C_X, then the line-of-sight angle ϕ_X is 0°. In addition, in the model M_X, if the location P_PP_X is identical to the location P_FP1_X, then the line-of-sight angle ϕ_X has a value (e.g.,)-60° corresponding to the maximum value ϕmax_X. In addition, in the model M_X, if the location P_PP_X is identical to the location P_FP2_X, then the line-of-sight angle ϕ_X has a value (e.g., +60°) corresponding to the maximum value ϕmax_X.

In addition, the line-of-sight angle calculating unit 21 calculates locations P_FP3_Y and P_FP4_Y in the Y-direction, using the above-described obtained eye feature point information. The location P_FP3_Y corresponds to the third feature point FP3 (i.e., the upper eyelid). The location P_FP4_Y corresponds to the fourth feature point FP4 (i.e., the lower eyelid).

Then, the line-of-sight angle calculating unit 21 calculates a location (hereinafter, referred to as "second reference location".) P_C_Y in the Y-direction, on the basis of the calculated locations P_FP3_Y and P_FP4_Y. The second reference location P_C_Y corresponds to an intermediate location between the third feature point FP3 and the fourth feature point FP4. Namely, the second reference location P_C_Y corresponds to a central portion of the area inside the palpebral fissure in the Y-direction.

Then, the line-of-sight angle calculating unit 21 calculates a location P_PP_Y in the Y-direction, using the above-described obtained pupil location information. The location P_PP_Y corresponds to the pupil location PP.

Figure 12:
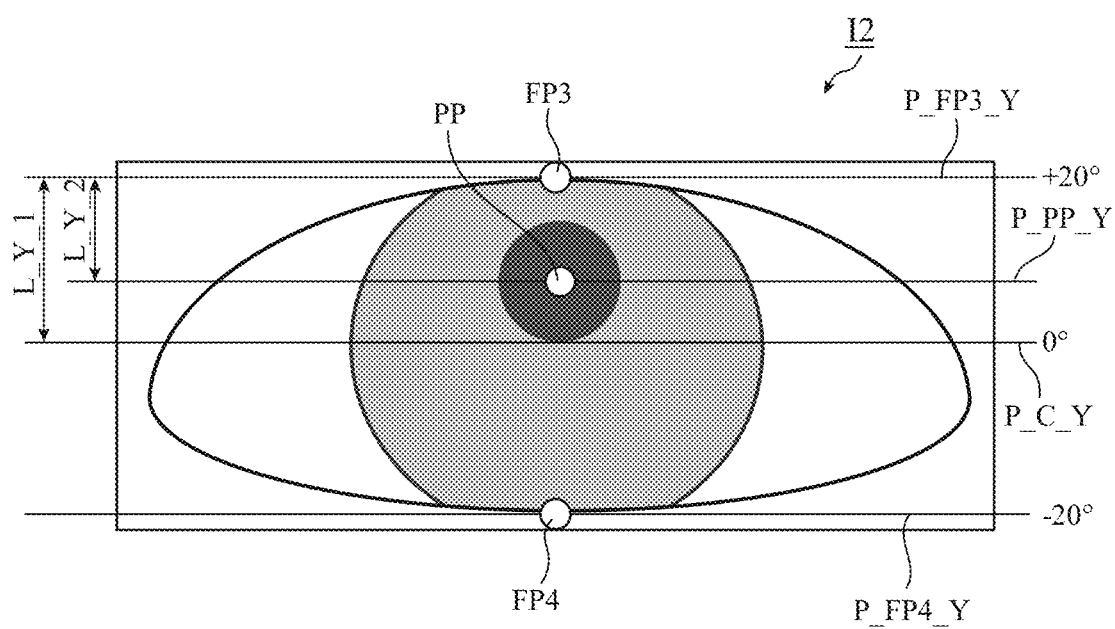
FIG. 12 is an explanatory diagram showing an example of a method of calculating a line-of-sight angle in a pitch direction.

Then, the line-of-sight angle calculating unit 21 calculates, for the location P_FP3_Y or the location P_FP4_Y, a distance L_Y_1 to the second reference location P_C_Y and a distance L_Y_2 to the location P_PP_Y. FIG. 12 shows an example of a case in which the location P_FP3_Y is used as a reference for the distances L_Y_1 and L_Y_2.

In the line-of-sight angle calculating unit 21 there is preset a value indicating a maximum value ϕmax_Y of the line-of-sight angle ϕ_Y. Using the set maximum value ϕmax_Y and the calculated distances L_Y_1 and L_Y_2, the line-of-sight angle calculating unit 21 calculates the line-of-sight angle ϕ_Y by the following equation (2).

$$\phi\_Y = \phi max\_Y \times (L\_Y\_1 - L\_Y\_2)/L\_Y\_1 \tag{2}$$

The maximum value ϕmax_Y is based on, for example, the following model M_Y. Specifically, in the model M_Y, if the location P_PP_Y is identical to the second reference location P_C_Y, then the line-of-sight angle ϕ_Y is 0°. In addition, in the model M_Y, if the location P_PP_Y is identical to the location P_FP3_Y, then the line-of-sight angle ϕ_Y has a value (e.g., +20°) corresponding to the maximum value ϕmax_Y. In addition, in the model M_Y, if the location P_PP_Y is identical to the location P_FP4_Y, then the line-of-sight angle ϕ_Y has a value (e.g., −20°) corresponding to the maximum value ϕmax_Y.

Note that the methods of calculating the line-of-sight angles ϕ_X and ϕ_Y are not limited to these specific examples. For the calculation of the line-of-sight angles ϕ_X and ϕ_Y, various publicly known techniques can be used. A detailed description of the techniques is omitted.

The line-of-sight direction detecting unit 22 obtains the face orientation information outputted from the face orientation estimating unit 13, and obtains the line-of-sight angle information outputted from the line-of-sight angle calculating unit 21. The line-of-sight direction detecting unit 22 detects a line-of-sight direction of the capturing target person, using the obtained face orientation information and the obtained line-of-sight angle information. The line-of-sight direction detecting unit 22 outputs information indicating the detected line-of-sight direction (hereinafter, referred to as "line-of-sight direction information".) to the occupant state determining unit 14.

More specifically, the line-of-sight direction detecting unit 22 calculates a vector V3 representing the line-of-sight direction of the capturing target person (hereinafter, referred to as "line-of-sight direction vector".), using the face orientation vector V1 calculated by the face orientation estimating unit 13 and the line-of-sight angle ϕ calculated by the line-of-sight angle calculating unit 21. The line-of-sight direction information includes the calculated line-of-sight direction vector V3. For the calculation of the line-of-sight direction vector V3, various publicly known techniques can be used. A detailed description of the techniques is omitted.

The occupant state determining unit 14 obtains the face orientation information outputted from the face orientation estimating unit 13, and obtains the line-of-sight direction information outputted from the line-of-sight direction detecting unit 22. The occupant state determining unit 14 determines whether or not the state of the capturing target person is a predetermined state (hereinafter, referred to as "alert target state".), using at least one of the obtained face orientation information and the obtained line-of-sight direction information. The occupant state determining unit 14 outputs information indicating a result of the determination (hereinafter, referred to as "determination result information".) to the alert output control unit 15.

For example, the alert target state includes a state in which the driver of the vehicle 1 is performing distracted driving (hereinafter, referred to as "distracted driving state".). A determination as to whether or not the state of the driver is a distracted driving state is made, for example, in the following manner.

Specifically, the occupant state determining unit 14 obtains information indicating a traveling direction of the vehicle 1. The information is obtained from, for example, a navigation system in the vehicle 1 or a sensor in the vehicle 1. The occupant state determining unit 14 calculates, using the obtained information, a vector V3' corresponding to a line-of-sight direction vector V3 obtained when the line of sight of the driver is directed in the traveling direction of the vehicle 1. The occupant state determining unit 14 determines whether or not the state of the driver is a distracted driving state, by comparing the calculated vector V3' with the line-of-sight direction vector V3 indicated by the obtained line-of-sight direction information.

In addition, for example, the alert target state includes a state in which the driver of the vehicle 1 does not check surroundings behind at timing at which the driver is supposed to check surroundings behind (hereinafter, referred to as "state of not paying attention to surroundings behind".). A determination as to whether or not the state of the driver is a state of not paying attention to surroundings behind is made, for example, in the following manner.

Specifically, the occupant state determining unit 14 obtains information indicating a location where a mirror for checking surroundings behind (e.g., a rear-view mirror or a side mirror) is set in the vehicle 1. The occupant state determining unit 14 calculates, using the obtained information, a vector V3" corresponding to a line-of-sight direction vector V3 obtained when the line of sight of the driver is directed to the mirror for checking surroundings behind.

In addition, the occupant state determining unit 14 obtains information indicating timing at which the driver of the vehicle 1 is supposed to check surroundings behind (e.g., timing at which the vehicle 1 makes a right turn or a left turn or changes lanes). The occupant state determining unit 14 determines whether or not the state of the driver is a state of not paying attention to surroundings behind, by comparing the calculated vector V3" with the line-of-sight direction vector V3 indicated by the obtained line-of-sight direction information at the timing indicated by the obtained information.

In addition, for example, the alert target state includes a state in which the attention level of the driver of the vehicle 1 is low (hereinafter, referred to as "low attention state".). A determination as to whether or not the state of the driver is a low attention state uses, for example, a result of determination as to a distracted driving state for a predetermined period of time or a result of determination as to a state of not paying attention to surroundings behind for a predetermined period of time.

In addition, for example, the alert target state includes a state in which the driver of the vehicle 1 is performing drowsy driving (hereinafter, referred to as "drowsy driving state".). A determination as to whether or not the state of the driver is a drowsy driving state uses, for example, the above-described obtained face orientation information.

In addition, for example, the alert target state includes a state in which driving by the driver of the vehicle 1 is impossible (hereinafter, referred to as "dead man state".). A determination as to whether or not the state of the driver is a dead man state uses, for example, the above-described obtained face orientation information.

In addition to those described above, for the determination for an alert target state, various publicly known techniques can be used. A detailed description of the techniques is omitted.

The alert output control unit 15 obtains the determination result information outputted from the occupant state determining unit 14. The alert output control unit 15 determines whether or not an alert needs to be outputted, using the obtained determination result information. When the alert output control unit 15 determines that an alert needs to be outputted, the alert output control unit 15 performs control to output an alert, using the output device 3.

For example, the alert output control unit 15 determines whether or not an image for alert (hereinafter, referred to as "alert image".) needs to be displayed, using the obtained determination result information. When the alert output control unit 15 determines that an alert image needs to be displayed, the alert output control unit 15 performs control to display an alert image, using the display included in the output device 3.

In addition, for example, the alert output control unit 15 determines whether or not a sound for alert (hereinafter, referred to as "alert sound".) needs to be outputted, using the obtained determination result information. When the alert output control unit 15 determines that an alert sound needs to be outputted, the alert output control unit 15 performs control to output an alert sound, using the speaker included in the output device 3.

In addition, for example, the alert output control unit 15 determines whether or not a signal for alert (hereinafter, referred to as "alert signal".) needs to be transmitted, using the obtained determination result information. When the alert output control unit 15 determines that an alert signal needs to be transmitted, the alert output control unit 15 performs control to transmit an alert signal, using the wireless communication device included in the output device 3.

The reference sign "F1" may be hereinafter used for a function of the captured-image obtaining unit 11. In addition, the reference sign "F2" may be used for a function of the face feature point extracting unit 12. In addition, the reference sign "F3" may be used for a function of the face orientation estimating unit 13. In addition, the reference sign "F4" may be used for a function of the occupant state determining unit 14. In addition, the reference sign "F5" may be used for a function of the alert output control unit 15.

The reference sign "F11" may be hereinafter used for a function of the line-of-sight angle calculating unit 21. In addition, the reference sign "F12" may be used for a function of the line-of-sight direction detecting unit 22.

The reference sign "F21" may be hereinafter used for a function of the eye area image obtaining unit 31. In addition, the reference sign "F22" may be used for a function of the luminance gradient calculating unit 32. In addition, the reference sign "F23" may be used for a function of the evaluation value calculating unit 33. In addition, the reference sign "F24" may be used for a function of the pupil location detecting unit 34.

Processes performed by the eye area image obtaining unit 31 may be hereinafter collectively referred to as "eye area image obtaining process". In addition, processes performed by the luminance gradient calculating unit 32 may be collectively referred to as "luminance gradient calculating process". In addition, processes performed by the evaluation value calculating unit 33 may be collectively referred to as "evaluation value calculating process". In addition, processes performed by the pupil location detecting unit 34 may be collectively referred to as "pupil location detecting process". In addition, processes performed by the pupil detection device 400 may be collectively referred to as "pupil detecting process". Namely, the pupil detecting process includes the eye area image obtaining process, the luminance gradient calculating process, the evaluation value calculating process, and the pupil location detecting process.

Processes performed by the line-of-sight angle calculating unit 21 may be hereinafter collectively referred to as "line-of-sight angle calculating process". In addition, processes performed by the line-of-sight direction detecting unit 22 may be collectively referred to as "line-of-sight direction detecting process". In addition, processes performed by the line-of-sight detection device 300 may be collectively referred to as "line-of-sight detecting process". Namely, the line-of-sight detecting process includes the pupil detecting process, the line-of-sight angle calculating process, and the line-of-sight direction detecting process.

Processes performed by the captured-image obtaining unit 11 may be hereinafter collectively referred to as "captured-image obtaining process". In addition, processes performed by the face feature point extracting unit 12 may be collectively referred to as "face feature point extracting process". In addition, processes performed by the face orientation estimating unit 13 may be collectively referred to as "face orientation estimating process". In addition, processes performed by the occupant state determining unit 14 may be collectively referred to as "occupant state determining process". In addition, processes and control performed by the alert output control unit 15 may be collectively referred to as "alert output control".

Next, with reference to FIGS. 13 to 15, hardware configurations of a main part of the occupant monitoring device 200 will be described.

Figure 13:
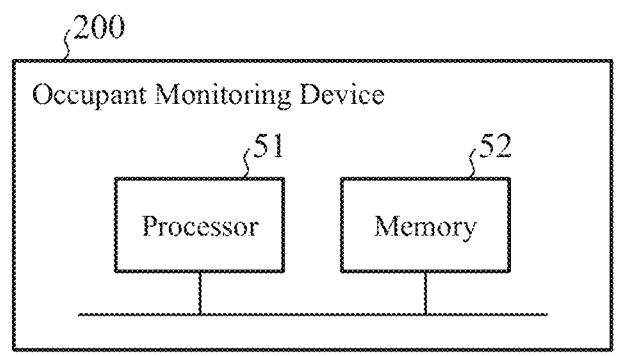
FIG. 13 is a block diagram showing a hardware configuration of a main part of an occupant monitoring device in the occupant monitoring system according to the first embodiment.

As shown in FIG. 13, the occupant monitoring device 200 includes a processor 51 and a memory 52. In the memory 52 there is stored a program corresponding to a plurality of functions F1 to F5, F11, F12, and F21 to F24. The processor 51 reads and executes the program stored in the memory 52. As a result, the plurality of functions F1 to F5, F11, F12, and F21 to F24 are implemented.

Figure 14:
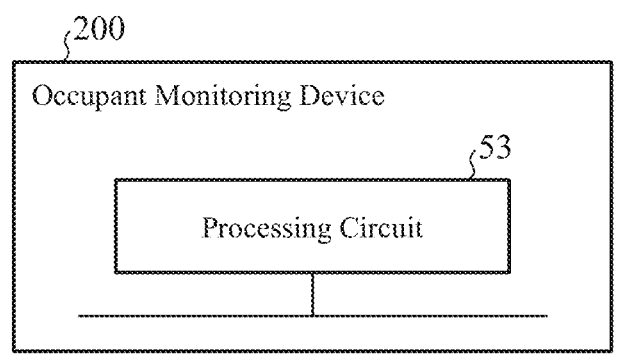
FIG. 14 is a block diagram showing another hardware configuration of the main part of the occupant monitoring device in the occupant monitoring system according to the first embodiment.

Alternatively, as shown in FIG. 14, the occupant monitoring device 200 includes a processing circuit 53. The processing circuit 53 performs processes corresponding to the plurality of functions F1 to F5, F11, F12, and F21 to F24. As a result, the plurality of functions F1 to F5, F11, F12, and F21 to F24 are implemented.

Figure 15:
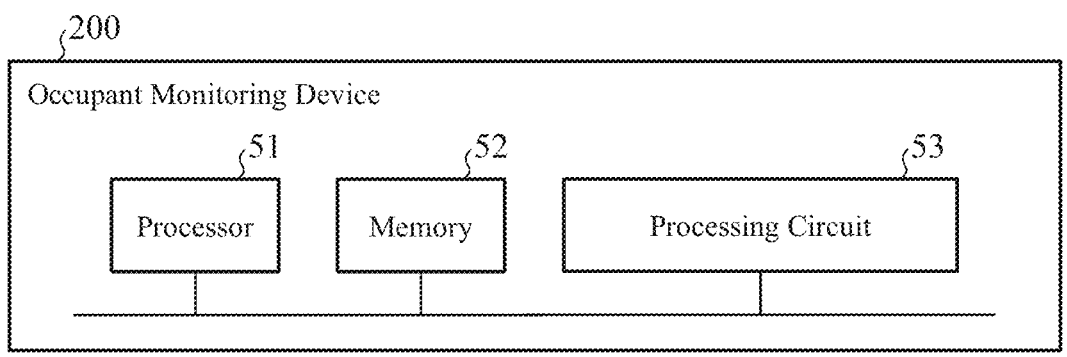
FIG. 15 is a block diagram showing another hardware configuration of the main part of the occupant monitoring device in the occupant monitoring system according to the first embodiment.

Alternatively, as shown in FIG. 15, the occupant monitoring device 200 includes a processor 51, a memory 52, and a processing circuit 53. In the memory 52 there is stored a program corresponding to some functions among the plurality of functions F1 to F5, F11, F12, and F21 to F24. The processor 51 reads and executes the program stored in the memory 52. As a result, the above-described some functions are implemented. In addition, the processing circuit 53 performs processes corresponding to the other functions among the plurality of functions F1 to F5, F11, F12, and F21 to F24. As a result, the above-described other functions are implemented.

The processor 51 includes one or more processors. Each individual processor uses, for example, a central processing unit (CPU), a graphics processing unit (GPU), a microprocessor, a microcontroller, or a digital signal processor (DSP).

The memory 52 includes one or more non-volatile memories. Alternatively, the memory 52 includes one or more non-volatile memories and one or more volatile memories. Namely, the memory 52 includes one or more memories. Each individual memory uses, for example, a semiconductor memory or a magnetic disk.

More specifically, each individual volatile memory uses, for example, a random access memory (RAM). In addition, each individual non-volatile memory uses, for example, a read only memory (ROM), a flash memory, an erasable programmable read only memory (EPROM), an electrically erasable programmable read only memory (EEPROM), a solid-state drive, or a hard disk drive.

The processing circuit 53 includes one or more digital circuits. Alternatively, the processing circuit 53 includes one or more digital circuits and one or more analog circuits. Namely, the processing circuit 53 includes one or more processing circuits. Each individual processing circuit uses, for example, an application specific integrated circuit (ASIC), a programmable logic device (PLD), a field-programmable gate array (FPGA), a system on a chip (SoC), or a system large-scale integration (LSI).

Here, when the processor 51 includes a plurality of processors, the plurality of functions F1 to F5, F11, F12, and F21 to F24 and the plurality of processors have any correspondence therebetween. Namely, each of the plurality of processors may read and execute a program corresponding to corresponding one or more functions among the plurality of functions F1 to F5, F11, F12, and F21 to F24.

In addition, when the memory 52 includes a plurality of memories, the plurality of functions F1 to F5, F11, F12, and F21 to F24 and the plurality of memories have any correspondence therebetween. Namely, each of the plurality of memories may store a program corresponding to corresponding one or more functions among the plurality of functions F1 to F5, F11, F12, and F21 to F24.

In addition, when the processing circuit 53 includes a plurality of processing circuits, the plurality of functions F1 to F5, F11, F12, and F21 to F24 and the plurality of processing circuits have any correspondence therebetween. Namely, each of the plurality of processing circuits may perform a process corresponding to corresponding one or more functions among the plurality of functions F1 to F5, F11, F12, and F21 to F24.

Figure 16:
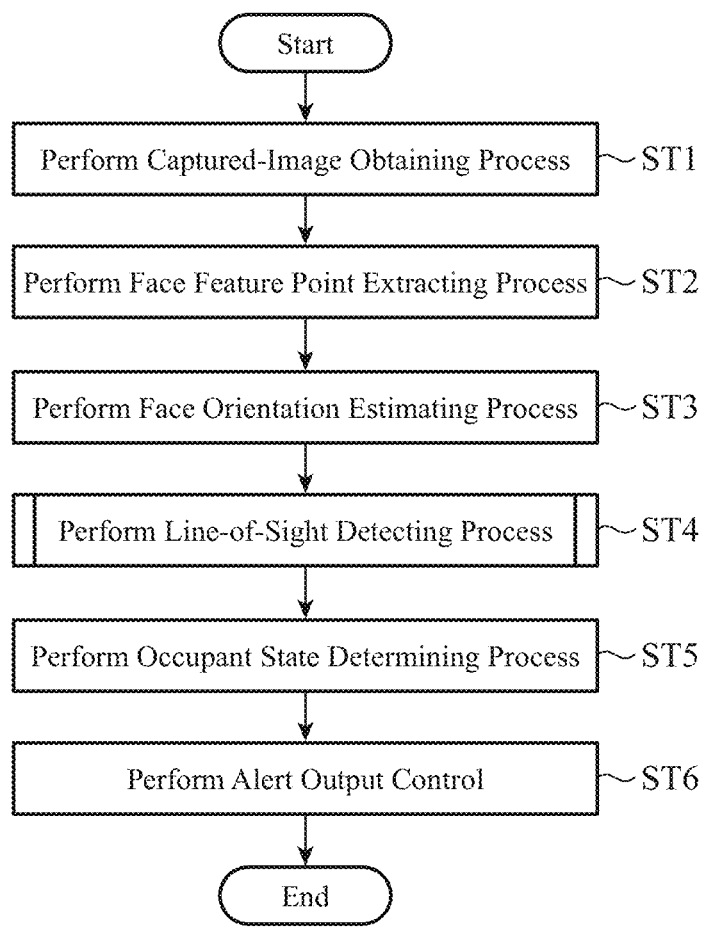
FIG. 16 is a flowchart showing the operations of the occupant monitoring device in the occupant monitoring system according to the first embodiment.

Next, with reference to a flowchart of FIG. 16, the operations of the occupant monitoring device 200 will be described. Processes shown in FIG. 16 are repeatedly performed when a predetermined condition is satisfied (e.g., an ignition power supply of the vehicle 1 is turned on).

First, the captured-image obtaining unit 11 performs a captured-image obtaining process (step ST1). Then, the face feature point extracting unit 12 performs a face feature point extracting process (step ST2). Then, the face orientation estimating unit 13 performs a face orientation estimating process (step ST3). Then, the line-of-sight detection device 300 performs a line-of-sight detecting process (step ST4).

Then, the occupant state determining unit 14 performs an occupant state determining process (step ST5). Then, the alert output control unit 15 performs alert output control (step ST6).

Figure 17:
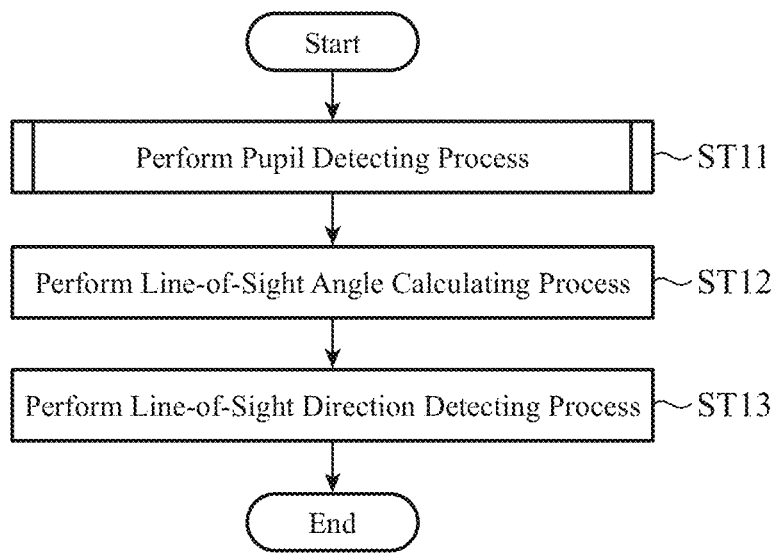
FIG. 17 is a flowchart showing the operations of a line-of-sight detection device in the occupant monitoring system according to the first embodiment.

Next, with reference to a flowchart of FIG. 17, the operations of the line-of-sight detection device 300 will be described. Namely, processes performed at step ST4 shown in FIG. 16 will be described.

First, the pupil detection device 400 performs a pupil detecting process (step ST11). Then, the line-of-sight angle calculating unit 21 performs a line-of-sight angle calculating process (step ST12). Then, the line-of-sight direction detecting unit 22 performs a line-of-sight direction detecting process (step ST13).

Figure 18:
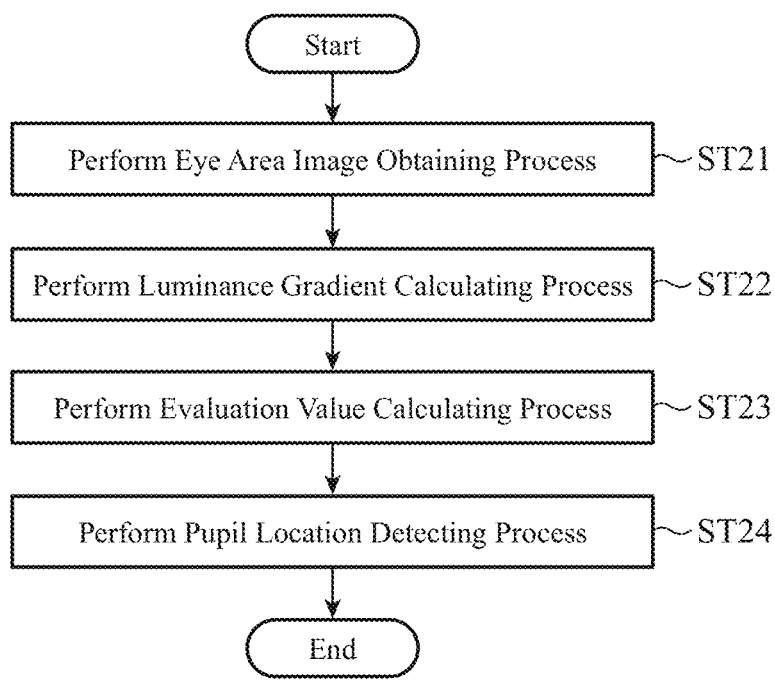
FIG. 18 is a flowchart showing the operations of the pupil detection device in the occupant monitoring system according to the first embodiment.

Next, with reference to a flowchart of FIG. 18, the operations of the pupil detection device 400 will be described. Namely, processes performed at step ST11 shown in FIG. 17 will be described.

First, the eye area image obtaining unit 31 performs an eye area image obtaining process (step ST21). Then, the luminance gradient calculating unit 32 performs a luminance gradient calculating process (step ST22). Then, the evaluation value calculating unit 33 performs an evaluation value calculating process (step ST23). Then, the pupil location detecting unit 34 performs a pupil location detecting process (step ST24).

Next, advantageous effects provided by the pupil detection device 400 will be described.

As described above, the conventional pupil detection device detects a corneal reflection image in a captured image, and detects a pupil location using the detected corneal reflection image. Hence, there is a problem that when a corneal reflection image is not detected normally, a pupil location cannot be detected.

Particularly, the DMS or OMS requires use of an inexpensive camera. Namely, a camera having a low resolution needs to be used. It is difficult to normally detect a corneal reflection image using such a camera. Hence, use of the conventional pupil detection device in the DMS or OMS causes a problem of unstable detection of a pupil location.

On the other hand, in the pupil detection device 400, upon detecting a pupil location PP, detection of a corneal reflection image is not required. Hence, regardless of whether or not it is a state in which a corneal reflection image is detected normally, a pupil location PP can be detected. As a result, even when the pupil detection device 400 is used in the occupant monitoring system 100, a pupil location PP can be stably detected.

In addition, upon detecting a pupil location PP, the pupil detection device 400 uses evaluation values E based on luminance gradient vectors V2. Thus, a pupil location PP can be detected with high accuracy. In addition, regardless of the size of a pupil of a line-of-sight detection target eye (i.e., regardless of the size of a pupil area in an eye area image I2), a pupil location PP can be detected.

In addition, in the pupil detection device 400, an evaluation area EA has a size smaller than the reference iris size. By reducing the size of the evaluation area EA, an increase in the speed of an evaluation value calculating process can be achieved. In addition, by an edge based on luminance discontinuity at a boundary portion between a pupil area and an iris area, a high evaluation value E can be calculated for an image unit U in the pupil area.

Next, a variant of the pupil detection device 400 will be described.

A part of the eye area image I2 corresponding to the outer corner of the eye is hereinafter referred to as "eye's outer corner portion". In addition, a part of the eye area image I2 corresponding to the inner corner of the eye is referred to as "eye's inner corner portion". In addition, a part of the eye area image I2 corresponding to the upper eyelid is referred to as "upper eyelid portion". In addition, a part of the eye area image I2 corresponding to the lower eyelid is referred to as "lower eyelid portion".

An area corresponding to a left-half portion of the evaluation area EA when the line-of-sight detection target eye is a left eye or an area corresponding to a right-half portion of the evaluation area EA when the line-of-sight detection target eye is a right eye is hereinafter referred to as "first portion evaluation area". In addition, an area corresponding to a right-half portion of the evaluation area EA when the line-of-sight detection target eye is a left eye or an area corresponding to a left-half portion of the evaluation area EA when the line-of-sight detection target eye is a right eye is referred to as "second portion evaluation area". In addition, an area corresponding to a lower-half portion of the evaluation area EA is referred to as "third portion evaluation area". In addition, an area corresponding to an upper-half portion of the evaluation area EA is referred to as "fourth portion evaluation area".

In a case in which the line-of-sight detection target eye is the left eye, when a focused image unit U_I in an evaluation value calculating process is located at the eye's outer corner portion, a state in which substantially the right-half portion of the evaluation area EA is located in an area outside the palpebral fissure can occur. In addition, in a case in which the line-of-sight detection target eye is the right eye, when a focused image unit U_I in an evaluation value calculating process is located at the eye's outer corner portion, a state in which substantially the left-half portion of the evaluation area EA is located in an area outside the palpebral fissure can occur.

In addition, in a case in which the line-of-sight detection target eye is the left eye, when a focused image unit U_I in an evaluation value calculating process is located at the eye's inner corner portion, a state in which substantially the left-half portion of the evaluation area EA is located in an area outside the palpebral fissure can occur. In addition, in a case in which the line-of-sight detection target eye is the right eye, when a focused image unit U_I in an evaluation value calculating process is located at the eye's inner corner portion, a state in which substantially the right-half portion of the evaluation area EA is located in an area outside the palpebral fissure can occur.

In addition, when a focused image unit U_I in an evaluation value calculating process is located at the upper eyelid portion, a state in which substantially the upper-half portion of the evaluation area EA is located in an area outside the palpebral fissure can occur. In addition, when a focused image unit U_I in an evaluation value calculating process is located at the lower eyelid portion, a state in which substantially the lower-half portion of the evaluation area EA is located in an area outside the palpebral fissure can occur.

In these states, a luminance gradient vector V2 corresponding to an image unit U in the area outside the palpebral fissure may be used for calculation of a first evaluation value E1. As a result, the accuracy of detection of a pupil location PP may decrease.

Hence, the first evaluation value calculating unit 41 may obtain eye feature point information outputted from the face feature point extracting unit 12. The first evaluation value calculating unit 41 may determine whether or not the focused image unit U_I is located at the eye's outer corner portion, using the obtained eye feature point information.

When the first evaluation value calculating unit 41 determines that the focused image unit U_I is located at the eye's outer corner portion, the first evaluation value calculating unit 41 may calculate a first evaluation value E1 using the first portion evaluation area, instead of the evaluation area EA.

In addition, the first evaluation value calculating unit 41 may determine whether or not the focused image unit U_I is located at the eye's inner corner portion, using the above-described obtained eye feature point information. When the first evaluation value calculating unit 41 determines that the focused image unit U_I is located at the eye's inner corner portion, the first evaluation value calculating unit 41 may calculate a first evaluation value E1 using the second portion evaluation area, instead of the evaluation area EA.

In addition, the first evaluation value calculating unit 41 may determine whether or not the focused image unit U_I is located at the upper eyelid portion, using the above-described obtained eye feature point information. When the first evaluation value calculating unit 41 determines that the focused image unit U_I is located at the upper eyelid portion, the first evaluation value calculating unit 41 may calculate a first evaluation value E1 using the third portion evaluation area, instead of the evaluation area EA.

In addition, the first evaluation value calculating unit 41 may determine whether or not the focused image unit U_I is located at the lower eyelid portion, using the eye feature point information. When the first evaluation value calculating unit 41 determines that the focused image unit U_I is located at the lower eyelid portion, the first evaluation value calculating unit 41 may calculate a first evaluation value E1 using the fourth portion evaluation area, instead of the evaluation area EA.

When the first portion evaluation area, the second portion evaluation area, the third portion evaluation area, or the fourth portion evaluation area is used for calculation of a first evaluation value E1, the first evaluation value E1 may be calculated as a value based on n/(N/2), instead of being calculated as a value based on n/N.

As a result, regardless of the location of a pupil of a line-of-sight detection target eye (i.e., regardless of the location of a pupil area in the eye area image I2), a pupil location PP can be detected. For example, even when the pupil is located at a location near the upper eyelid, a pupil location PP can be detected.

Next, another variant of the pupil detection device 400 will be described.

The luminance gradient calculating unit 32 may calculate a value (hereinafter, referred to as "luminance gradient value".) ΔB corresponding to the magnitude of a luminance gradient vector V2, using a first luminance gradient value ΔB_X and a second luminance gradient value ΔB_Y. Luminance gradient information may include the calculated luminance gradient values ΔB.

The first evaluation value calculating unit 41 may compare luminance gradient values ΔB of luminance gradient vectors V2 corresponding to respective individual evaluation image units U_E with a predetermined threshold value ΔBth. The first evaluation value calculating unit 41 may exclude luminance gradient vectors V2 each having a luminance gradient value ΔB less than or equal to the threshold value ΔBth from calculation of a first evaluation value E1.

As a result, unnecessary luminance gradient vectors V2 can be excluded from calculation of a first evaluation value E1. Specifically, for example, while luminance gradient vectors V2 corresponding to the above-described edge are included in calculation of first evaluation values E1, other luminance gradient vectors V2 can be excluded from calculation of first evaluation values E1. As a result, while a pupil location PP is detected with high accuracy, an increase in the speed of an evaluation value calculating process can be achieved.

Figure 19:
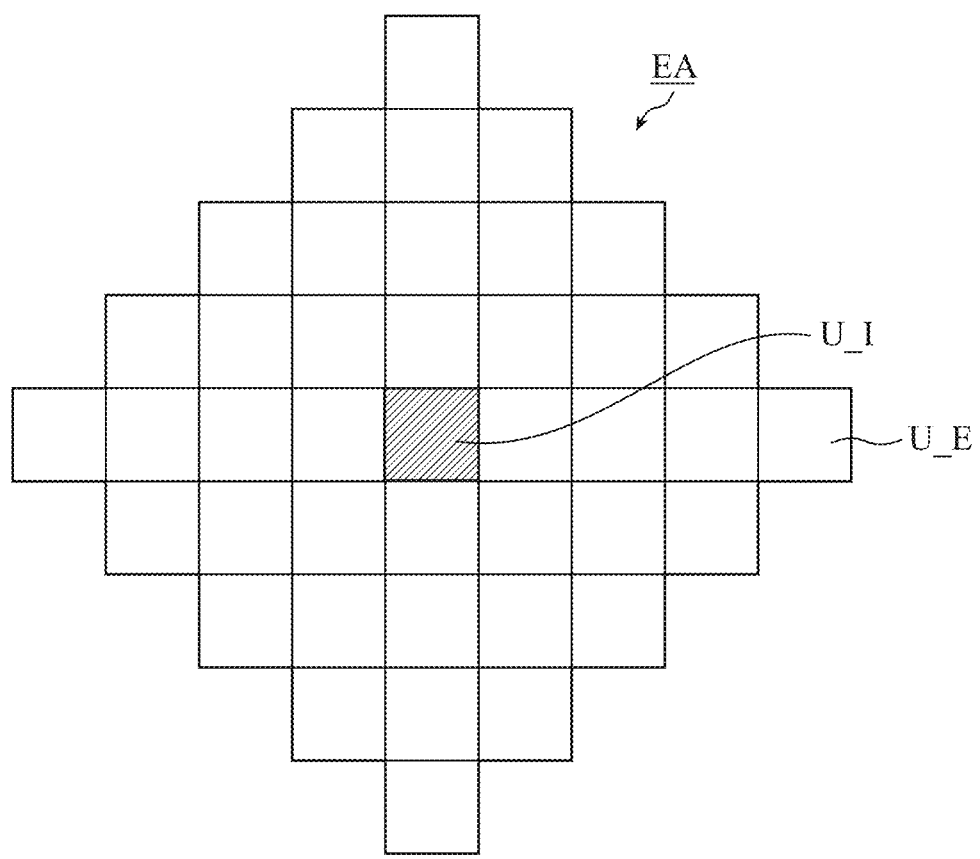
FIG. 19 is an explanatory diagram showing another example of the evaluation area.

Next, with reference to FIG. 19, another variant of the pupil detection device 400 will be described.

The shape of an evaluation area EA is not limited to a square shape. The evaluation area EA may have any shape. For example, the shape of the evaluation area EA may be a rhombus shape or a circular shape (see FIG. 19).

Next, with reference to FIGS. 20 to 27, variants of the occupant monitoring system 100 will be described.

An in-vehicle information device 4 may be mounted on the vehicle 1. In addition, a portable information terminal 5 may be carried in the vehicle 1. The in-vehicle information device 4 and the portable information terminal 5 may communicate freely with each other. The in-vehicle information device 4 may communicate freely with a server 6 outside the vehicle 1. The portable information terminal 5 may communicate freely with the server 6 outside the vehicle 1.

The camera 2 may be one provided in the in-vehicle information device 4 or the portable information terminal 5. In addition, the output device 3 may be one provided in the in-vehicle information device 4 or the portable information terminal 5. In addition, each of the plurality of functions F1 to F5, F11, F12, and F21 to F24 may be implemented by the in-vehicle information device 4, or may be implemented by the portable information terminal 5, or may be implemented by the server 6, or may be implemented by the in-vehicle information device 4 and the portable information terminal 5 cooperating with each other, or may be implemented by the in-vehicle information device 4 and the server 6 cooperating with each other, or may be implemented by the portable information terminal 5 and the server 6 cooperating with each other.

Figure 20:
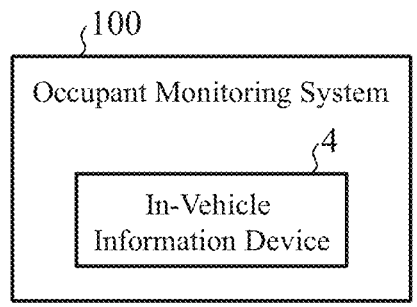
FIG. 20 is a block diagram showing a system configuration of the occupant monitoring system according to the first embodiment.
Figure 21:
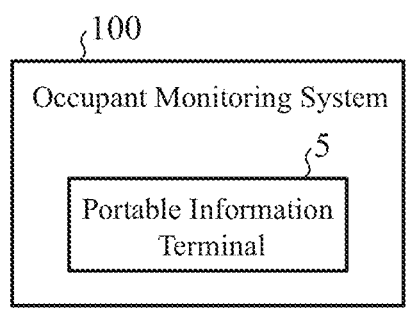
FIG. 21 is a block diagram showing another system configuration of the occupant monitoring system according to the first embodiment.
Figure 22:
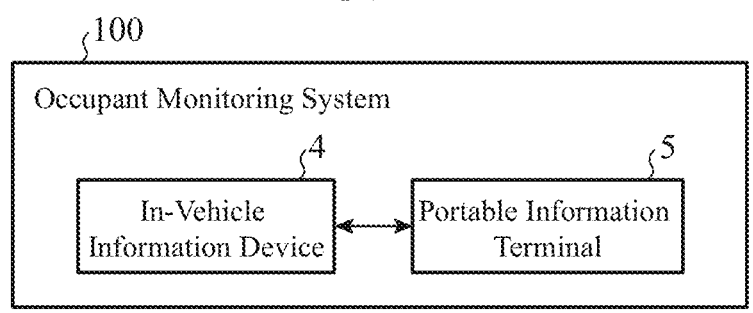
FIG. 22 is a block diagram showing another system configuration of the occupant monitoring system according to the first embodiment.
Figure 23:
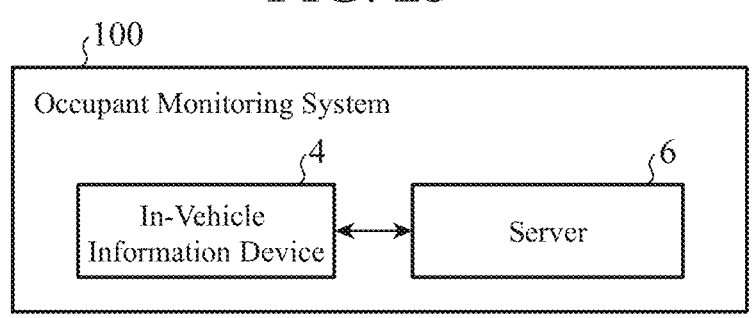
FIG. 23 is a block diagram showing another system configuration of the occupant monitoring system according to the first embodiment.
Figure 24:
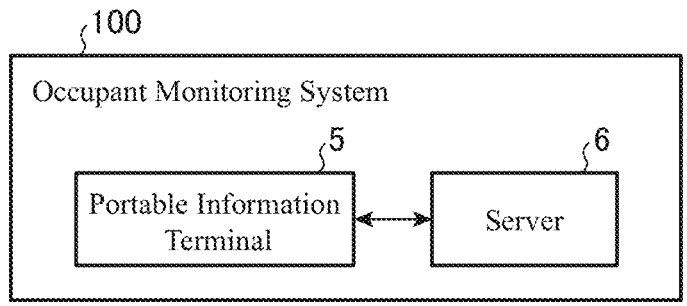
FIG. 24 is a block diagram showing another system configuration of the occupant monitoring system according to the first embodiment.
Figure 25:
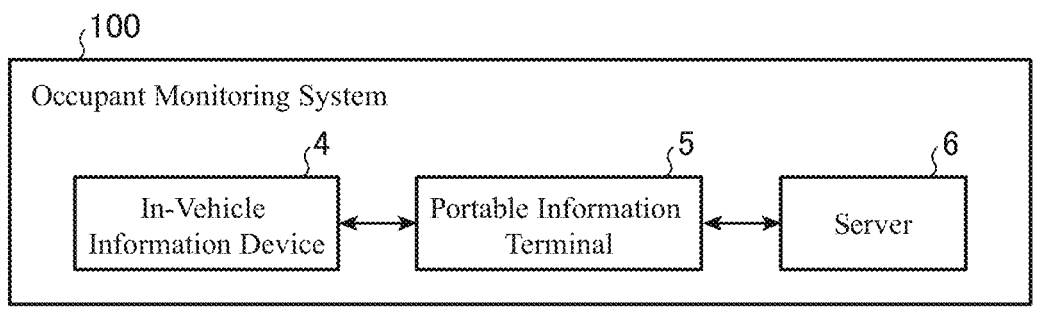
FIG. 25 is a block diagram showing another system configuration of the occupant monitoring system according to the first embodiment.
Figure 26:
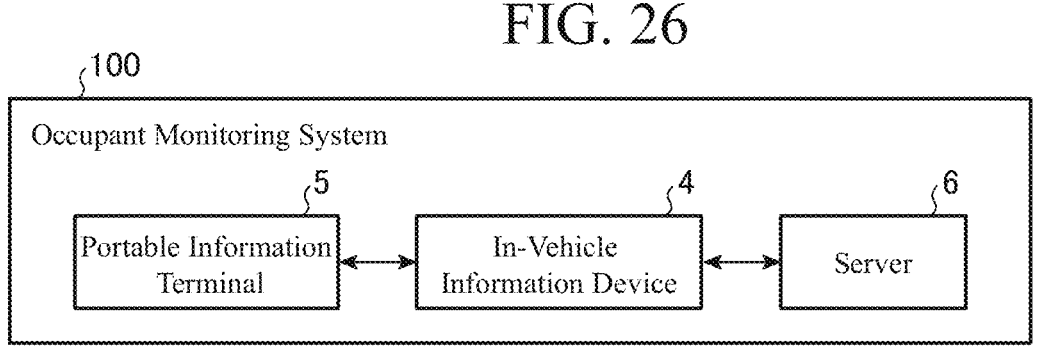
FIG. 26 is a block diagram showing another system configuration of the occupant monitoring system according to the first embodiment.
Figure 27:
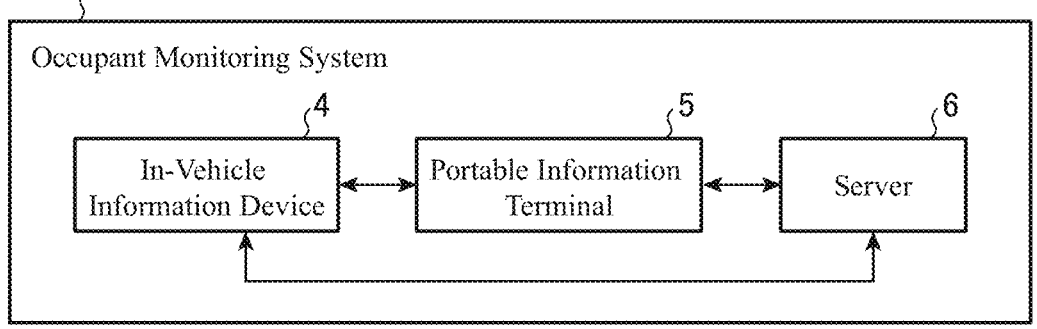
FIG. 27 is a block diagram showing another system configuration of the occupant monitoring system according to the first embodiment.

Namely, as shown in FIG. 20, a main part of the occupant monitoring system 100 may include the in-vehicle information device 4. Alternatively, as shown in FIG. 21, the main part of the occupant monitoring system 100 may include the portable information terminal 5. Alternatively, as shown in FIG. 22, the main part of the occupant monitoring system 100 may include the in-vehicle information device 4 and the portable information terminal 5. Alternatively, as shown in FIG. 23, the main part of the occupant monitoring system 100 may include the in-vehicle information device 4 and the server 6. Alternatively, as shown in FIG. 24, the main part of the occupant monitoring system 100 may include the portable information terminal 5 and the server 6. Alternatively, as shown in FIG. 25, 26, or 27, the main part of the occupant monitoring system 100 may include the in-vehicle information device 4, the portable information terminal 5, and the server 6.

As described above, the pupil detection device 400 according to the first embodiment includes the eye area image obtaining unit 31 that obtains image data (second image data) representing an eye area image I2 in a captured image I1 obtained by the camera 2; the luminance gradient calculating unit 32 that calculates luminance gradient vectors V2 corresponding to respective individual image units U in the eye area image I2, using the image data (second image data); the evaluation value calculating unit 33 that calculates evaluation values E corresponding to the respective individual image units U, using the luminance gradient vectors V2; and the pupil location detecting unit 34 that detects a pupil location PP in the eye area image I2, using the evaluation values E. By this configuration, upon detecting a pupil location PP, the need to detect a corneal reflection image can be eliminated. As a result, even when the camera 2 having a low resolution is used, the pupil location PP can be stably detected. In addition, the pupil location PP can be detected with high accuracy.

In addition, the line-of-sight detection device 300 according to the first embodiment includes the pupil detection device 400; the line-of-sight angle calculating unit 21 that calculates a line-of-sight angle ϕ on the basis of a pupil location PP; and the line-of-sight direction detecting unit 22 that detects a line-of-sight direction on the basis of the line-of-sight angle ϕ. By this configuration, even when the camera 2 having a low resolution is used, a line-of-sight direction can be stably detected.

In addition, the occupant monitoring system 100 according to the first embodiment includes the line-of-sight detection device 300; the occupant state determining unit 14 that determines whether or not the state of an occupant (capturing target person) of the vehicle 1 is an alert target state, on the basis of a line-of-sight direction; and the alert output control unit 15 that performs control to output an alert on the basis of a result of the determination by the occupant state determining unit 14. By this configuration, even when the camera 2 having a low resolution is used, an alert target state can be stably detected.

In addition, a pupil detection method according to the first embodiment includes step ST21 at which the eye area image obtaining unit 31 obtains image data (second image data) representing an eye area image I2 in a captured image I1 obtained by the camera 2; step ST22 at which the luminance gradient calculating unit 32 calculates luminance gradient vectors V2 corresponding to respective individual image units U in the eye area image I2, using the image data (second image data); step ST23 at which the evaluation value calculating unit 33 calculates evaluation values E corresponding to the respective individual image units U, using the luminance gradient vectors V2; and step ST24 at which the pupil location detecting unit 34 detects a pupil location PP in the eye area image I2, using the evaluation values E. By this configuration, upon detecting a pupil location PP, the need to detect a corneal reflection image can be eliminated. As a result, even when the camera 2 having a low resolution is used, the pupil location PP can be stably detected. In addition, the pupil location PP can be detected with high accuracy.

Second Embodiment

Figure 28:
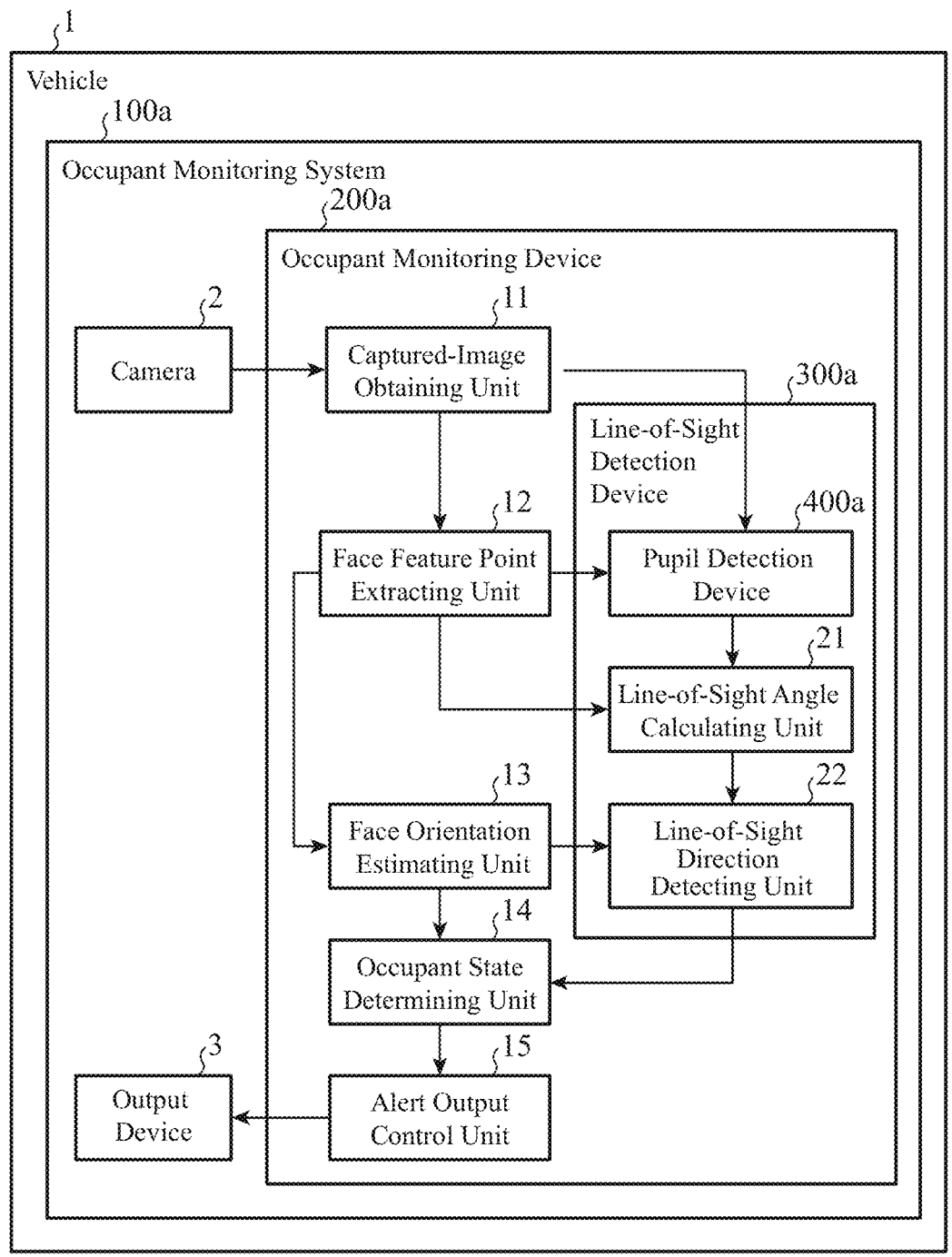
FIG. 28 is a block diagram showing a main part of an occupant monitoring system according to a second embodiment.
Figure 29:
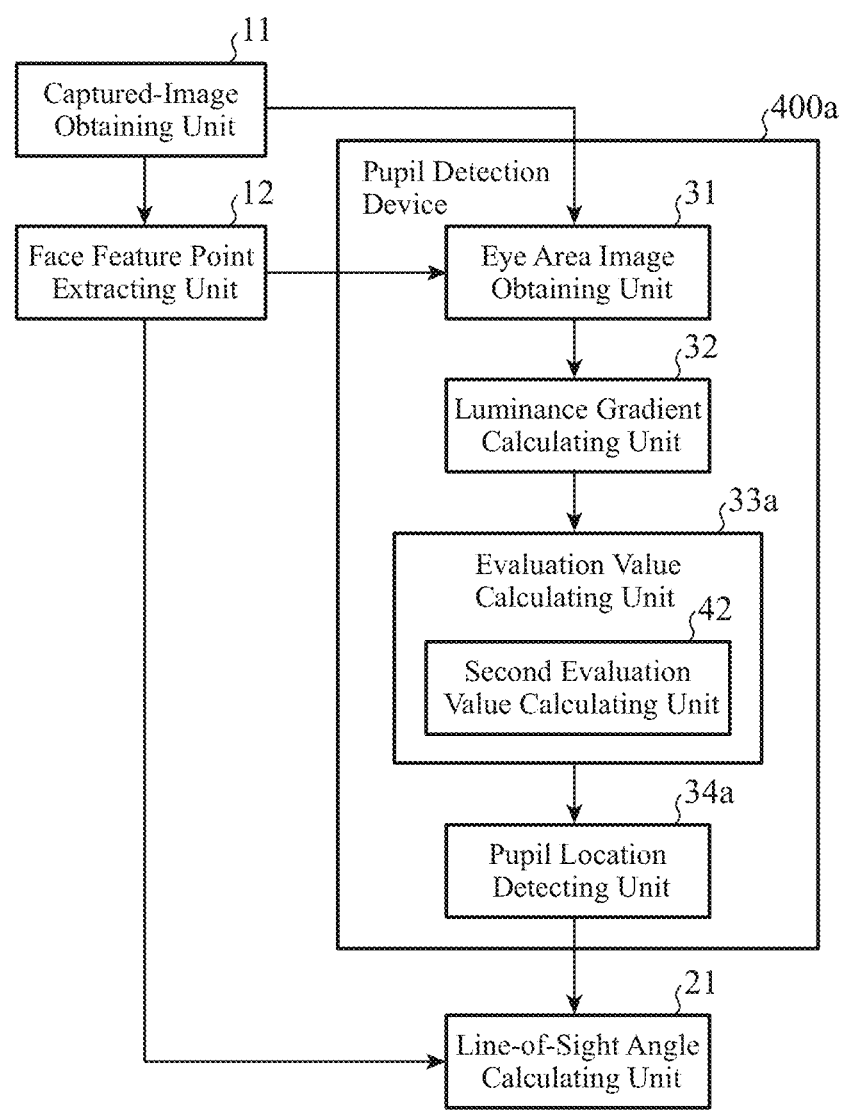
FIG. 29 is a block diagram showing a main part of a pupil detection device in the occupant monitoring system according to the second embodiment.

FIG. 28 is a block diagram showing a main part of an occupant monitoring system according to a second embodiment. FIG. 29 is a block diagram showing a main part of a pupil detection device in the occupant monitoring system according to the second embodiment. With reference to FIGS. 28 and 29, the occupant monitoring system according to the second embodiment will be described. Note that in FIG. 28, the same blocks as those shown in FIG. 1 are given the same reference signs and description thereof is omitted. Note also that in FIG. 29, the same blocks as those shown in FIG. 2 are given the same reference signs and description thereof is omitted.

As shown in FIG. 28, an occupant monitoring system 100a includes the camera 2, the output device 3, and an occupant monitoring device 200a. The occupant monitoring device 200a includes the captured-image obtaining unit 11, the face feature point extracting unit 12, the face orientation estimating unit 13, the occupant state determining unit 14, the alert output control unit 15, and a line-of-sight detection device 300a. The line-of-sight detection device 300a includes the line-of-sight angle calculating unit 21, the line-of-sight direction detecting unit 22, and a pupil detection device 400a. As shown in FIG. 29, the pupil detection device 400a includes the eye area image obtaining unit 31, the luminance gradient calculating unit 32, an evaluation value calculating unit 33a, and a pupil location detecting unit 34a. The evaluation value calculating unit 33a includes a second evaluation value calculating unit 42.

The evaluation value calculating unit 33a obtains luminance gradient information outputted from the luminance gradient calculating unit 32. The evaluation value calculating unit 33a calculates evaluation values E corresponding to respective individual image units U in an eye area image I2, using the obtained luminance gradient information. The evaluation value calculating unit 33a outputs information including the calculated evaluation values E (i.e., evaluation value information) to the pupil location detecting unit 34a.

Figure 30:
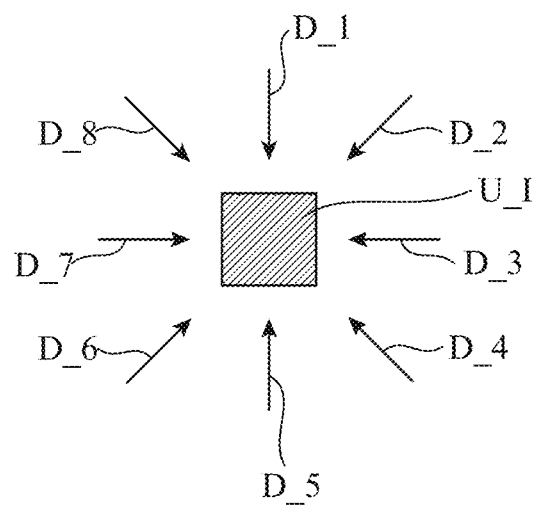
FIG. 30 is an explanatory diagram showing an example of a plurality of directions.

Here, the evaluation values E calculated by the evaluation value calculating unit 33a each include a second evaluation value E2 calculated by the second evaluation value calculating unit 42. Namely, the evaluation value information includes the calculated second evaluation values E2. The second evaluation values E2 are each based on the number m of directions of luminance gradient vectors V2 directed toward a corresponding one of the individual image units U (i.e., a focused image unit U_I). With reference to FIG. 30, a method of calculating a second evaluation value E2 will be described.

First, the second evaluation value calculating unit 42 sets an evaluation area EA including a focused image unit U_I. The evaluation area EA is the same as that described in the first embodiment. Thus, repetitive description is omitted.

In the second evaluation value calculating unit 42 there are preset M directions D_1 to D_M oriented toward the focused image unit U_I. M is any integer greater than or equal to 2. FIG. 30 shows an example of directions D_1 to D_8 for a case of M=8. As shown in FIG. 30, the directions D1 to D_8 are set to directions obtained by dividing 360° into eight equal parts. Namely, the directions D_1 to D_8 are set to directions spaced at 45° intervals.

The above-described obtained luminance gradient information includes, for each of N luminance gradient vectors V2 corresponding to N evaluation image units U_E, a luminance gradient angle θ corresponding to the direction of the corresponding one of the N luminance gradient vectors V2. Using the luminance gradient angles θ, the second evaluation value calculating unit 42 determines, for each of the M directions D_1 to D_M, whether or not there is a luminance gradient vector V2 directed toward the focused image unit U_I in an orientation corresponding to the direction D. By this determination, the second evaluation value calculating unit 42 calculates the number m of directions of luminance gradient vectors V2 directed toward the focused image unit U_I. Namely, m is calculated as a value between 0 and M, inclusive.

Then, the second evaluation value calculating unit 42 calculates a second evaluation value E2 based on the calculated number m of directions. Namely, the second evaluation value E2 is calculated as a larger value for a larger number m of directions. In other words, the second evaluation value E2 is calculated as a smaller value for a smaller number m of directions.

For example, in a case of M=8 (see FIG. 30), it is assumed that N luminance gradient vectors V2 include luminance gradient vectors V2 directed toward the focused image unit U_I in orientations corresponding to the directions D_1 and D_2, and do not include luminance gradient vectors V2 directed toward the focused image unit U_I in orientations corresponding to the directions D_3 to D_8. In this case, the number m of directions is calculated as 2 by the second evaluation value calculating unit 42. In addition, the second evaluation value calculating unit 42 calculates a second evaluation value E2 based on the calculated number m of directions. For example, a second evaluation value E2 based on m/M is calculated.

The pupil location detecting unit 34a obtains the evaluation value information outputted from the evaluation value calculating unit 33a. The pupil location detecting unit 34a detects a pupil location PP in the eye area image I2, using the obtained evaluation value information. The pupil location detecting unit 34a outputs information indicating the detected pupil location PP (i.e., pupil location information) to the line-of-sight angle calculating unit 21.

Specifically, the pupil location detecting unit 34a detects the largest value among a plurality of second evaluation values E2 corresponding to a plurality of image units U in the eye area image I2. In other words, the pupil location detecting unit 34a detects the maximum value of the plurality of second evaluation values E2. The pupil location detecting unit 34a detects coordinate values C_X and C_Y indicating the location of an image unit U corresponding to the detected maximum value. As a result, the coordinate values CX and C_Y corresponding to a pupil location PP are detected.

Principles of detecting a pupil location PP by detection of the largest value (i.e., the maximum value) are the same as those described in the first embodiment. Hence, repetitive description is omitted.

The reference sign "F23a" may be hereinafter used for a function of the evaluation value calculating unit 33a. In addition, the reference sign "F24a" may be used for a function of the pupil location detecting unit 34a.

Processes performed by the evaluation value calculating unit 33a may be hereinafter collectively referred to as "evaluation value calculating process". In addition, processes performed by the pupil location detecting unit 34a may be collectively referred to as "pupil location detecting process".

Hardware configurations of a main part of the occupant monitoring device 200a are the same as those described with reference to FIGS. 13 to 15 in the first embodiment. Hence, a detailed description is omitted. Namely, the occupant monitoring device 200a has a plurality of functions F1 to F5, F11, F12, F21, F22, F23a, and F24a. Each of the plurality of functions F1 to F5, F11, F12, F21, F22, F23a, and F24a may be implemented by the processor 51 and the memory 52 or may be implemented by the processing circuit 53.

The operations of the occupant monitoring device 200a are the same as those described with reference to the flowchart of FIG. 16 in the first embodiment. Hence, repetitive description is omitted.

The operations of the line-of-sight detection device 300a are the same as those described with reference to the flowchart of FIG. 17 in the first embodiment. Hence, repetitive description is omitted.

Figure 31:
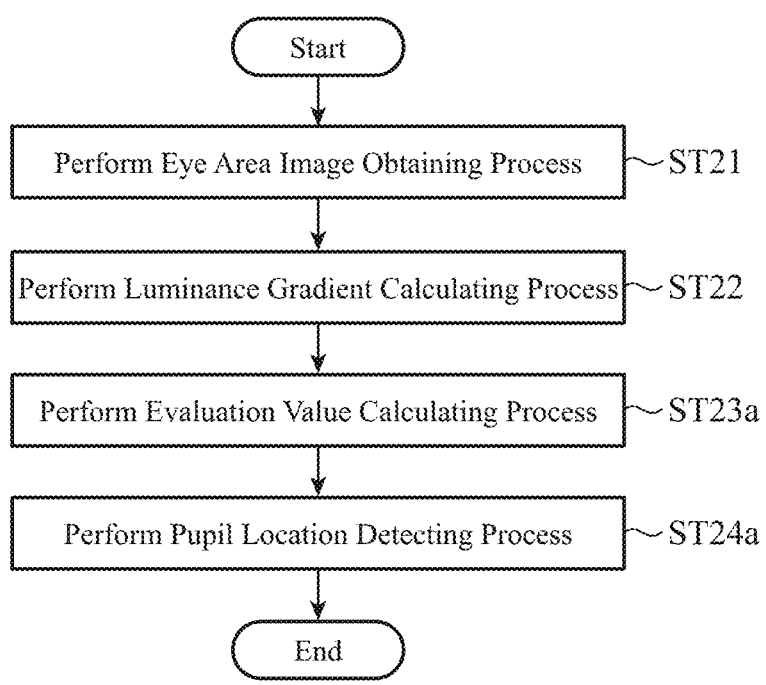
FIG. 31 is a flowchart showing the operations of the pupil detection device in the occupant monitoring system according to the second embodiment.

Next, with reference to a flowchart of FIG. 31, the operations of the pupil detection device 400a will be described. Note that in FIG. 31, the same steps as those shown in FIG. 18 are given the same reference signs and description thereof is omitted.

First, processes at steps ST21 and ST22 are performed. Then, the evaluation value calculating unit 33a performs an evaluation value calculating process (step ST23a). Then, the pupil location detecting unit 34a performs a pupil location detecting process (step ST24a).

Note that the pupil detection device 400a can adopt the same various variants as those described in the first embodiment. In addition, the occupant monitoring system 100a can adopt the same various variants as those described in the first embodiment.

For example, when the second evaluation value calculating unit 42 determines that a focused image unit U_I is located at an eye's outer corner portion, the second evaluation value calculating unit 42 may calculate a second evaluation value E2 using a first portion evaluation area. In addition, when the second evaluation value calculating unit 42 determines that a focused image unit U_I is located at an eye's inner corner portion, the second evaluation value calculating unit 42 may calculate a second evaluation value E2 using a second portion evaluation area. In addition, when the second evaluation value calculating unit 42 determines that a focused image unit U_I is located at an upper eyelid portion, the second evaluation value calculating unit 42 may calculate a second evaluation value E2 using a third portion evaluation area. In addition, when the second evaluation value calculating unit 42 determines that a focused image unit U_I is located at a lower eyelid portion, the second evaluation value calculating unit 42 may calculate a second evaluation value E2 using a fourth portion evaluation area.

When the first portion evaluation area, the second portion evaluation area, the third portion evaluation area, or the fourth portion evaluation area is used for calculation of a second evaluation value E2, the second evaluation value E2 may be calculated as a value based on m/(M/2), instead of being calculated as a value based on m/M.

In addition, for example, the second evaluation value calculating unit 42 may exclude luminance gradient vectors V2 each having a luminance gradient value $\Delta B$ less than or equal to a threshold value $\Delta Bth$ from calculation of a second evaluation value E2.

As described above, in the pupil detection device 400a according to the second embodiment, an evaluation value E includes a second evaluation value E2 based on the number m of directions of luminance gradient vectors V2 directed toward a corresponding one of individual image units U. Upon detecting a pupil location PP with high accuracy, first evaluation values E1 can, of course, be used and second evaluation values E2 can also be used.

Third Embodiment

Figure 32:
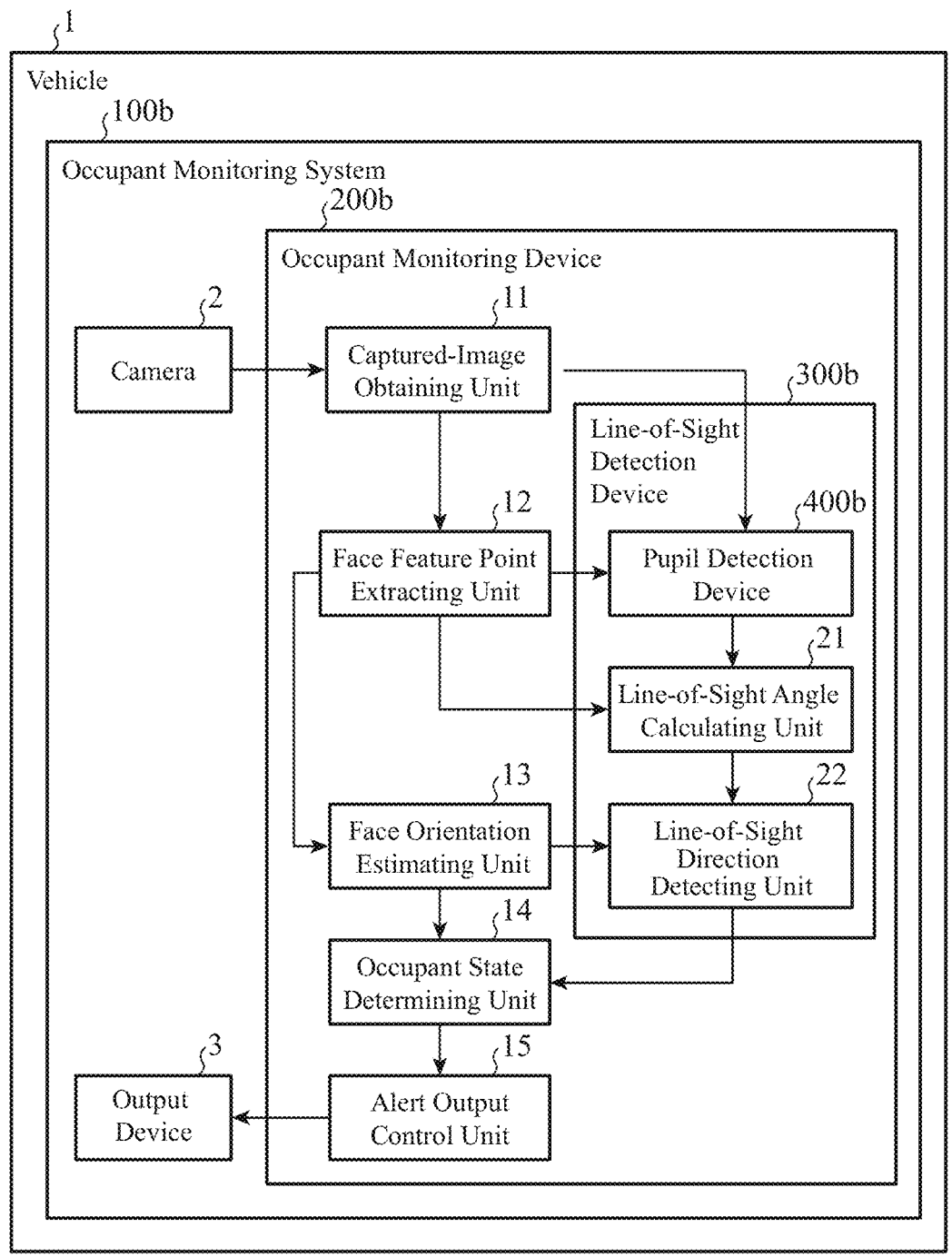
FIG. 32 is a block diagram showing a main part of an occupant monitoring system according to a third embodiment.
Figure 33:
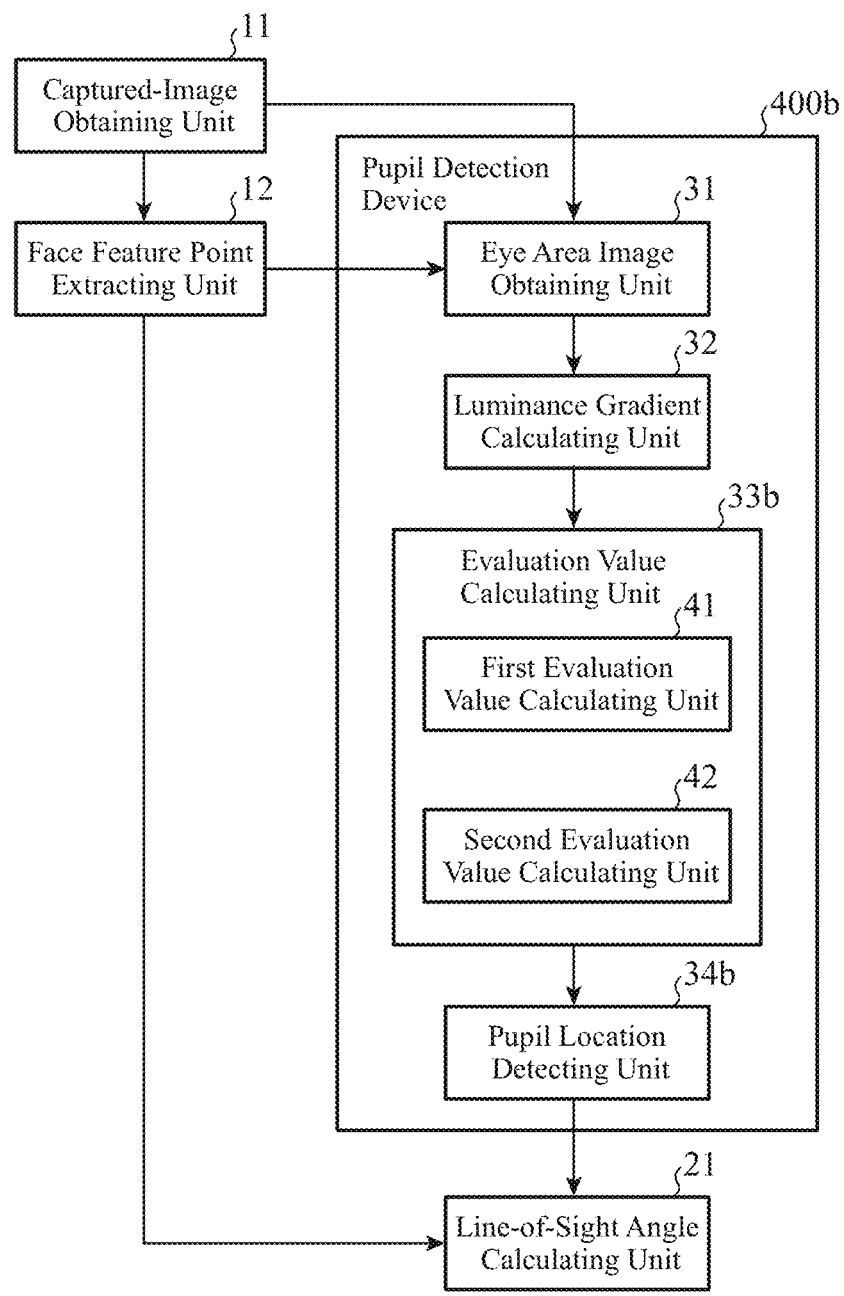
FIG. 33 is a block diagram showing a main part of a pupil detection device in the occupant monitoring system according to the third embodiment.

FIG. 32 is a block diagram showing a main part of an occupant monitoring system according to a third embodiment. FIG. 33 is a block diagram showing a main part of a pupil detection device in the occupant monitoring system according to the third embodiment. With reference to FIGS. 32 and 33, the occupant monitoring system according to the third embodiment will be described. Note that in FIG. 32, the same blocks as those shown in FIG. 1 are given the same reference signs and description thereof is omitted. Note also that in FIG. 33, the same blocks as those shown in FIG. 2 are given the same reference signs and description thereof is omitted.

As shown in FIG. 32, an occupant monitoring system 100b includes the camera 2, the output device 3, and an occupant monitoring device 200b. The occupant monitoring device 200b includes the captured-image obtaining unit 11, the face feature point extracting unit 12, the face orientation estimating unit 13, the occupant state determining unit 14, the alert output control unit 15, and a line-of-sight detection device 300b. The line-of-sight detection device 300b includes the line-of-sight angle calculating unit 21, the line-of-sight direction detecting unit 22, and a pupil detection device 400b. As shown in FIG. 33, the pupil detection device 400b includes the eye area image obtaining unit 31, the luminance gradient calculating unit 32, an evaluation value calculating unit 33b, and a pupil location detecting unit 34b. The evaluation value calculating unit 33b includes the first evaluation value calculating unit 41 and the second evaluation value calculating unit 42.

The evaluation value calculating unit 33b obtains luminance gradient information outputted from the luminance gradient calculating unit 32. The evaluation value calculating unit 33b calculates evaluation values E corresponding to respective individual image units U in an eye area image I2, using the obtained luminance gradient information. The evaluation value calculating unit 33b outputs information including the calculated evaluation values E (i.e., evaluation value information) to the pupil location detecting unit 34b.

Here, the evaluation values E calculated by the evaluation value calculating unit 33b each include a first evaluation value E1 calculated by the first evaluation value calculating unit 41, and a second evaluation value E2 calculated by the second evaluation value calculating unit 42. Namely, the evaluation value information includes the calculated first evaluation values E1 and the calculated second evaluation values E2.

A method of calculating a first evaluation value E1 is the same as that described in the first embodiment. Hence, repetitive description is omitted. In addition, a method of calculating a second evaluation value E2 is the same as that described in the second embodiment. Hence, repetitive description is omitted.

The pupil location detecting unit 34b obtains the evaluation value information outputted from the evaluation value calculating unit 33b. The pupil location detecting unit 34b detects a pupil location PP in an eye area image I2, using the obtained evaluation value information. The pupil location detecting unit 34b outputs information indicating the detected pupil location PP (i.e., pupil location information) to the line-of-sight angle calculating unit 21. Three methods of detecting a pupil location PP by the pupil location detecting unit 34b will be described below.

<First Detection Method>

In the pupil location detecting unit 34b there is preset a predetermined reference value E1ref. The pupil location detecting unit 34b detects image units U corresponding to first evaluation values E1 greater than or equal to the reference value E1ref among a plurality of image units U included in an eye area image I2. Then, the pupil location detecting unit 34b detects an image unit U whose corresponding second valuation value E2 is the largest value among the detected image units U. Namely, the pupil location detecting unit 34b detects an image unit U whose corresponding second evaluation value E2 is the maximum value. Then, the pupil location detecting unit 34b detects coordinate values C_X and C_Y indicating the location of the detected image unit U. As a result, the coordinate values C_X and C_Y corresponding to a pupil location PP are detected.

Principles of detecting a pupil location PP by detection of the largest value (i.e., the maximum value) are the same as those described in the first embodiment. Hence, repetitive description is omitted.

<Second Detection Method>

In the pupil location detecting unit 34b there is preset a predetermined reference value E2ref. The pupil location detecting unit 34b detects image units U corresponding to second evaluation values E2 greater than or equal to the reference value E2ref among a plurality of image units U included in an eye area image I2. Then, the pupil location detecting unit 34b detects an image unit U whose corresponding first valuation value E1 is the largest value among the detected image units U. Namely, the pupil location detecting unit 34b detects an image unit U whose corresponding first evaluation value E1 is the maximum value. Then, the pupil location detecting unit 34b detects coordinate values C_X and C_Y indicating the location of the detected image unit U. As a result, the coordinate values C_X and C_Y corresponding to a pupil location PP are detected.

Principles of detecting a pupil location PP by detection of the largest value (i.e., the maximum value) are the same as those described in the first embodiment. Hence, repetitive description is omitted.

<Third Detection Method>

The pupil location detecting unit 34b calculates, for each individual image unit U in an eye area image I2, a statistical value S of a corresponding first evaluation value E1 and a corresponding second evaluation value E2. The pupil location detecting unit 34b detects an image unit U whose corresponding statistical value S is the largest value among a plurality of image units U included in the eye area image I2. Namely, the pupil location detecting unit 34b detects an image unit U whose corresponding statistical value S is the maximum value. The pupil location detecting unit 34b detects coordinate values C_X and C_Y indicating the location of the detected image unit U. As a result, the coordinate values C_X and C_Y corresponding to a pupil location PP are detected.

Principles of detecting a pupil location PP by detection of the largest value (i.e., the maximum value) are the same as those described in the first embodiment. Hence, repetitive description is omitted.

A statistical value S uses, for example, a total value of a corresponding first evaluation value E1 and a corresponding second evaluation value E2 (S=E1+E2). Alternatively, for example, a statistical value S uses a total value of a value E1' obtained by weighting a corresponding first evaluation value E1 with a predetermined weight value W1, and a corresponding second evaluation value E2 (S=E1'+E2). Alternatively, for example, a statistical value S uses a total value of a corresponding first evaluation value E1 and a value E2' obtained by weighting a corresponding second evaluation value E2 with a predetermined weight value W2 (S=E1+E2'). Alternatively, for example, a statistical value S uses a total value of a value E1' obtained by weighting a corresponding first evaluation value E1 with a predetermined weight value W1, and a value E2' obtained by weighting a corresponding second evaluation value E2 with a predetermined weight value W2 (S=E1'+E2').

The reference sign "F23b" may be hereinafter used for a function of the evaluation value calculating unit 33b. In addition, the reference sign "F24b" may be used for a function of the pupil location detecting unit 34b.

Processes performed by the evaluation value calculating unit 33b may be hereinafter collectively referred to as "evaluation value calculating process". In addition, processes performed by the pupil location detecting unit 34b may be collectively referred to as "pupil location detecting process".

Hardware configurations of a main part of the occupant monitoring device 200b are the same as those described with reference to FIGS. 13 to 15 in the first embodiment. Hence, a detailed description is omitted. Namely, the occupant monitoring device 200b has a plurality of functions F1 to F5, F11, F12, F21, F22, F23b, and F24b. Each of the plurality of functions F1 to F5, F11, F12, F21, F22, F23b, and F24b may be implemented by the processor 51 and the memory 52 or may be implemented by the processing circuit 53.

The operations of the occupant monitoring device 200b are the same as those described with reference to the flowchart of FIG. 16 in the first embodiment. Hence, repetitive description is omitted.

The operations of the line-of-sight detection device 300b are the same as those described with reference to the flowchart of FIG. 17 in the first embodiment. Hence, repetitive description is omitted.

Figure 34:
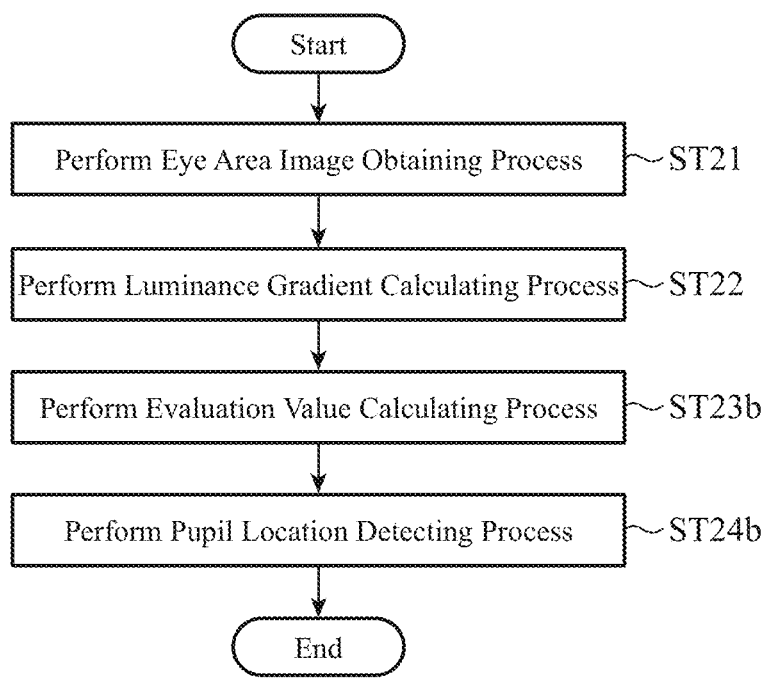
FIG. 34 is a flowchart showing the operations of the pupil detection device in the occupant monitoring system according to the third embodiment.

Next, with reference to a flowchart of FIG. 34, the operations of the pupil detection device 400b will be described. Note that in FIG. 34, the same steps as those shown in FIG. 18 are given the same reference signs and description thereof is omitted.

First, processes at steps ST21 and ST22 are performed. Then, the evaluation value calculating unit 33b performs an evaluation value calculating process (step ST23b). Then, the pupil location detecting unit 34b performs a pupil location detecting process (step ST24b).

Note that the pupil detection device 400b can adopt the same various variants as those described in the first embodiment. In addition, the occupant monitoring system 100b can adopt the same various variants as those described in the first embodiment.

For example, when the evaluation value calculating unit 33b determines that a focused image unit U_I is located at an eye's outer corner portion, the evaluation value calculating unit 33b may calculate a first evaluation value E1 and a second evaluation value E2 using a first portion evaluation area. In addition, when the evaluation value calculating unit 33b determines that a focused image unit U_I is located at an eye's inner corner portion, the evaluation value calculating unit 33b may calculate a first evaluation value E1 and a second evaluation value E2 using a second portion evaluation area. In addition, when the evaluation value calculating unit 33b determines that a focused image unit U_I is located at an upper eyelid portion, the evaluation value calculating unit 33b may calculate a first evaluation value E1 and a second evaluation value E2 using a third portion evaluation area. In addition, when the evaluation value calculating unit 33b determines that a focused image unit U_I is located at a lower eyelid portion, the evaluation value calculating unit 33b may calculate a first evaluation value E1 and a second evaluation value E2 using a fourth portion evaluation area.

In addition, for example, the evaluation value calculating unit 33b may exclude luminance gradient vectors V2 each having a luminance gradient value ΔB less than or equal to a threshold value ΔBth from calculation of a first evaluation value E1 and a second evaluation value E2.

As described above, in the pupil detection device 400b according to the third embodiment, an evaluation value E includes a first evaluation value E1 based on the number n of luminance gradient vectors V2 directed toward a corresponding one of individual image units U, and includes a second evaluation value E2 based on the number m of directions of luminance gradient vectors V2 directed toward the corresponding one of the individual image units U. Upon detecting a pupil location PP with high accuracy, first evaluation values E1 can, of course, be used and second evaluation values E2 can also be used.

Note that in the disclosure of the present application, a free combination of the embodiments, modifications to any component of each of the embodiments, or omissions of any component in each of the embodiments are possible that fall within the scope of the disclosure.

INDUSTRIAL APPLICABILITY

Pupil detection devices, line-of-sight detection devices, and pupil detection methods according to the present disclosure can be used in, for example, occupant monitoring systems. Occupant monitoring systems according to the present disclosure can be used in, for example, vehicles.

REFERENCE SIGNS LIST

1: vehicle, 2: camera, 3: output device, 4: in-vehicle information device, 5: portable information terminal, 6: server, 11: captured-image obtaining unit, 12: face feature point extracting unit, 13: face orientation estimating unit, 14: occupant state determining unit, 15: alert output control unit, 21: line-of-sight angle calculating unit, 22: line-of-sight direction detecting unit, 31: eye area image obtaining unit, 32: luminance gradient calculating unit, 33, 33a, 33b: evaluation value calculating unit, 34, 34a, 34b: pupil location detecting unit, 41: first evaluation value calculating unit, 42: second evaluation value calculating unit, 51: processor, 52: memory, 53: processing circuit, 100, 100a, 100b: occupant monitoring system, 200, 200a, 200b: occupant monitoring device, 300, 300a, 300b: line-of-sight detection device, and 400, 400a, 400b: pupil detection device.

The invention claimed is:

1. A pupil detection device comprising:
processing circuitry
to obtain image data representing an eye area image in an image captured by a camera, the eye area image including a plurality of image units arranged in an X-direction and a Y-direction orthogonal to each other, each of the image units including one or more pixels adjacent to each other;
to calculate luminance gradient vectors corresponding to the respective individual image units in the eye area image, using a difference value between luminance values of two image units in the X-direction and a difference value between luminance values of two image units in the Y-direction;
to calculate evaluation values corresponding to the respective individual image units, using a luminance gradient angle corresponding to the direction of each of the luminance gradient vectors; and
to detect a pupil location in the eye area image, using the evaluation values.

2. The pupil detection device according to claim 1, wherein each of the evaluation values includes a first evaluation value based on the number of luminance gradient vectors directed toward a corresponding one of the individual image units.

3. The pupil detection device according to claim 2, wherein the processing circuitry detects the pupil location by detecting a location of one of the image units which corresponds to a maximum value of the first evaluation value.

4. The pupil detection device according to claim 1, wherein each of the evaluation values includes a second evaluation value based on the number of directions of luminance gradient vectors directed toward a corresponding one of the individual image units.

5. The pupil detection device according to claim 4, wherein the processing circuitry detects the pupil location by detecting a location of one of the image units which corresponds to a maximum value of the second evaluation value.

6. The pupil detection device according to claim 1, wherein each of the evaluation values includes a first evaluation value based on the number of luminance gradient vectors directed toward a corresponding one of the individual image units, and includes a second evaluation value based on the number of directions of luminance gradient vectors directed toward the corresponding one of the individual image units.

7. The pupil detection device according to claim 6, wherein the processing circuitry detects the pupil location by detecting a location of an image unit corresponding to a maximum value of the second evaluation value among at least one of the image units which corresponds to the first evaluation value greater than or equal to a reference value.

8. The pupil detection device according to claim 6, wherein the processing circuitry detects the pupil location by detecting a location of an image unit corresponding to a maximum value of the first evaluation value among at least one of the image units which corresponds to the second evaluation value greater than or equal to a reference value.

9. The pupil detection device according to claim 6, wherein the processing circuitry detects the pupil location by detecting a location of one of the image units which corresponds to a maximum value of a statistical value of the first evaluation value and the second evaluation value.

10. The pupil detection device according to claim 9, wherein the statistical value is based on at least one of a value obtained by weighting the first evaluation value and a value obtained by weighting the second evaluation value.

11. The pupil detection device according to claim 1, wherein the processing circuitry excludes one of the luminance gradient vectors which has a magnitude less than or equal to a threshold value from the calculation of the evaluation values.

12. The pupil detection device according to claim 1, wherein the processing circuitry calculates each of the evaluation values using at least one of the luminance gradient vectors which is in an evaluation area corresponding to a corresponding one of the individual image units.

13. The pupil detection device according to claim 12, wherein when the processing circuitry calculates one of the evaluation values which corresponds to one of the image units which is in an eye's outer corner portion of the eye area image, the processing circuitry calculates the one of the evaluation values using at least one of the luminance gradient vectors which is in a first portion evaluation area corresponding to a left-half portion or a right-half portion of the evaluation area.

14. The pupil detection device according to claim 12, wherein when the processing circuitry calculates one of the evaluation values which corresponds to one of the image units which is in an eye's inner corner portion of the eye area image, the processing circuitry calculates the one of the evaluation values using at least one of the luminance gradient vectors which is in a second portion evaluation area corresponding to a right-half portion or a left-half portion of the evaluation area.

15. The pupil detection device according to claim 12, wherein when the processing circuitry calculates one of the evaluation values which corresponds to one of the image units which is in an upper eyelid portion of the eye area image, the processing circuitry calculates the one of the evaluation values using at least one of the luminance gradient vectors which is in a third portion evaluation area corresponding to a lower-half portion of the evaluation area.

16. The pupil detection device according to claim 12, wherein when the processing circuitry calculates one of the evaluation values which corresponds to one of the image units which is in a lower eyelid portion of the eye area image, the processing circuitry calculates the one of the evaluation values using at least one of the luminance gradient vectors which is in a fourth portion evaluation area corresponding to an upper-half portion of the evaluation area.

17. The pupil detection device according to claim 12, wherein the evaluation area has a size smaller than a reference iris size.

18. A line-of-sight detection device comprising:
the pupil detection device according to claim 1; and
processing circuitry to calculate a line-of-sight angle on a basis of the pupil location; and
to detect a line-of-sight direction on a basis of the line-of-sight angle.

19. An occupant monitoring system comprising:
the line-of-sight detection device according to claim 18; and
processing circuitry to determine whether or not a state of an occupant of a vehicle is an alert target state, on a basis of the line-of-sight direction; and
to perform control to output an alert on a basis of a result of the determination.

20. A pupil detection method comprising:
obtaining image data representing an eye area image in an image captured by a camera, the eye area image including a plurality of image units arranged in an X-direction and a Y-direction orthogonal to each other, each of the image units including one or more pixels adjacent to each other;
calculating luminance gradient vectors corresponding to the respective individual image units in the eye area image, using a difference value between luminance values of two image units in the X-direction and a difference value between luminance values of two image units in the Y-direction;
calculating evaluation values corresponding to the respective individual image units, using a luminance gradient angle corresponding to the direction of each of the luminance gradient vectors; and
detecting a pupil location in the eye area image, using the evaluation values.

* * * * *